(12) United States Patent
Hynynen et al.

(10) Patent No.: US 12,318,637 B2
(45) Date of Patent: Jun. 3, 2025

(54) SYSTEMS AND METHODS FOR REDUCING THERMAL SKULL-INDUCED ABERRATIONS DURING TRANSCRANIAL ULTRASOUND THERAPEUTIC PROCEDURES

(71) Applicant: SUNNYBROOK RESEARCH INSTITUTE, Toronto (CA)

(72) Inventors: Kullervo Hynynen, Toronto (CA); Alec Hughes, Mississauga (CA); Lulu Deng, Toronto (CA)

(73) Assignee: SUNNYBROOK RESEARCH INSTITUTE, Ontario (CA)

( * ) Notice: Subject to any disclaimer, the term of this patent is extended or adjusted under 35 U.S.C. 154(b) by 0 days.

(21) Appl. No.: 17/613,654

(22) PCT Filed: May 28, 2020

(86) PCT No.: PCT/CA2020/050731
§ 371 (c)(1),
(2) Date: Nov. 23, 2021

(87) PCT Pub. No.: WO2020/237382
PCT Pub. Date: Dec. 3, 2020

(65) Prior Publication Data
US 2022/0233890 A1 Jul. 28, 2022

Related U.S. Application Data

(60) Provisional application No. 62/855,283, filed on May 31, 2019.

(51) Int. Cl.
*A61N 7/02* (2006.01)
*A61B 6/03* (2006.01)
(Continued)

(52) U.S. Cl.
CPC .............. *A61N 7/02* (2013.01); *A61B 6/03* (2013.01); *A61B 6/501* (2013.01); *A61B 8/0808* (2013.01);
(Continued)

(58) Field of Classification Search
CPC ............. A61N 7/02; A61N 2007/0073; A61N 2007/0078; A61N 2007/0095; A61B 6/03;
(Continued)

(56) References Cited

U.S. PATENT DOCUMENTS 5,606,972 A * 3/1997 Routh ................. G01S 15/8979
600/455
6,042,556 A * 3/2000 Beach ...................... A61N 7/02
601/3
(Continued)

FOREIGN PATENT DOCUMENTS

WO 2016170427 A1 10/2016
WO 2019069135 A1 4/2019

OTHER PUBLICATIONS

Aarnio et al., "A New Ultrasound Method for Determining the Acoustic Phase Shifts Cause by the Skull Bone", Ultrasound in Med. & Biol., vol. 31, No. 6, pp. 771-780, 2005 (Year: 2005).*
(Continued)

*Primary Examiner* — Adil Partap S Virk
(74) *Attorney, Agent, or Firm* — Stephen Leonard; AIRD & MCBURNEY LP

(57) ABSTRACT

Various example embodiments of the present disclosure provide systems and methods for the dynamic correction and reduction of thermal variations in skull-induced aberrations during a focused ultrasound therapy procedure. Unlike conventional approaches involving static corrections for skull-induced aberrations, various example embodiments of the present disclosure employ ultrasound detection and a skull
(Continued)

thickness estimate from volumetric image data to intermittently and dynamically determine corrections for skull-induced aberrations, such that aberration correction reduction is updated intraoperatively and maintained despite local thermally-induced changes in the speed of sound of the local skull region due to intraoperative intracranial heating. Furthermore, in some example embodiments, a measure dependent on the speed of sound with the skull is intraoperatively determined and compared to a previously determined value of the measure to determine a change in the skull temperature, based on a pre-determined relationship between changes in the measure and changes in skull temperature.

22 Claims, 15 Drawing Sheets

(51) Int. Cl.
*A61B 6/50* (2024.01)
*A61B 8/00* (2006.01)
*A61B 8/08* (2006.01)
*A61N 7/00* (2006.01)
*G01S 7/52* (2006.01)
*G01S 15/89* (2006.01)

(52) U.S. Cl.
CPC .......... *A61B 8/0858* (2013.01); *A61B 8/0875* (2013.01); *A61B 8/4227* (2013.01); *A61B 8/4477* (2013.01); *A61B 8/4488* (2013.01); *A61B 8/5207* (2013.01); *A61B 8/5261* (2013.01); *A61N 2007/0073* (2013.01); *A61N 2007/0078* (2013.01); *A61N 2007/0095* (2013.01); *G01S 7/52049* (2013.01); *G01S 15/899* (2013.01)

(58) Field of Classification Search
CPC ..... A61B 6/501; A61B 8/0808; A61B 8/0858; A61B 8/0875; A61B 8/4227; A61B 8/4477; A61B 8/4488; A61B 8/5207; A61B 8/5261; G01S 7/52049; G01S 15/899
See application file for complete search history.

(56) References Cited

U.S. PATENT DOCUMENTS

| | | | | |
|---|---|---|---|---|
| 8,852,103 | B2* | 10/2014 | Rothberg | A61N 7/02 600/459 |
| 9,939,413 | B2* | 4/2018 | Angelsen | A61B 8/485 |
| 2002/0111552 | A1 | 8/2002 | Maor et al. | |
| 2003/0092987 | A1* | 5/2003 | Hynynen | A61N 7/02 600/437 |
| 2004/0122323 | A1* | 6/2004 | Vortman | A61N 7/02 600/459 |
| 2004/0210134 | A1* | 10/2004 | Hynynen | A61B 8/485 601/2 |
| 2004/0236222 | A1* | 11/2004 | Mao | A61B 8/481 600/458 |
| 2009/0054780 | A1* | 2/2009 | Yang | G10K 11/346 367/105 |
| 2009/0112096 | A1* | 4/2009 | Tamura | G01S 7/52077 600/454 |
| 2009/0306502 | A1* | 12/2009 | Lacoste | A61B 8/4236 600/439 |
| 2010/0022886 | A1* | 1/2010 | Ayati | A61B 5/6822 600/454 |
| 2010/0125193 | A1* | 5/2010 | Zadicario | A61B 90/37 600/323 |
| 2011/0270136 | A1 | 11/2011 | Vitek et al. | |
| 2012/0209150 | A1* | 8/2012 | Zeng | A61N 7/02 601/2 |
| 2013/0144165 | A1* | 6/2013 | Ebbini | A61B 8/0891 600/439 |
| 2013/0338485 | A1* | 12/2013 | Mougenot | A61B 8/0858 600/411 |
| 2014/0074076 | A1* | 3/2014 | Gertner | A61B 6/12 606/169 |
| 2014/0350439 | A1* | 11/2014 | Zur | G01R 33/385 601/3 |
| 2015/0148675 | A1* | 5/2015 | Haupt | A61B 8/488 600/438 |
| 2016/0317121 | A1* | 11/2016 | Frenz | A61B 8/14 |
| 2017/0188992 | A1* | 7/2017 | O'Brien | A61B 8/488 |
| 2018/0177491 | A1 | 6/2018 | Hynynen et al. | |
| 2018/0214123 | A1* | 8/2018 | Takano | G01S 7/52025 |
| 2018/0220998 | A1* | 8/2018 | Imai | A61B 8/543 |
| 2018/0353157 | A1* | 12/2018 | Eibl | A61B 8/5246 |
| 2019/0000416 | A1 | 1/2019 | Hynynen | |
| 2019/0021666 | A1 | 1/2019 | Hynynen | |
| 2019/0030375 | A1 | 1/2019 | Zachar | |
| 2019/0159761 | A1* | 5/2019 | Erkamp | A61B 8/06 |
| 2019/0175954 | A1* | 6/2019 | Levy | A61B 8/585 |
| 2019/0307427 | A1* | 10/2019 | Levy | A61B 6/5217 |
| 2020/0187910 | A1* | 6/2020 | Pinton | A61B 8/085 |
| 2021/0007713 | A1* | 1/2021 | Matsui | G01S 15/8906 |
| 2021/0330294 | A1 | 10/2021 | Hynynen et al. | |

OTHER PUBLICATIONS

Meral et al., "128 Element Ultrasound Array for Transcranial Imaging", 2010, 2010 IEEE International Ultrasonics Symposium (Year: 2010).*
Clement et al., "Correlation of Ultrasound Phase with Physical Skull Properties", 2002 (Year: 2002).*
Conner et al., "Patterns of Thermal Deposition in the Skull During Transcranial Focused Ultrasound Surgery", 2004 (Year: 2004).*
J. Aarnio, G. T. Clement and K. Hynynen, "Investigation of ultrasound phase shifts caused by the skull bone using low-frequency reflection data," 2001 IEEE Ultrasonics Symposium. Proceedings. An International Symposium (Cat. No.01CH37263), 2001, pp. 1503-1506 vol. 2, doi: 10.1109/ULTSYM.2001.992005.
Clement, G. T. et al., "A non-invasive method for focusing ultrasound through the human skull", Phys. Med. Biol. 47 (2002) 1219-1236.
Clement, G. T. et al., "Correlation of Ultrasound Phase with Physical Skull Properties", Ultrasound in Med. & Biol., vol. 28, No. 5, pp. 617-624, 2002.
Hughes, A. et al., "Design of patient-specific focused ultrasound arrays for non-invasive brain therapy with increased trans-skull transmission and steering range", Phys Med Biol.; 62(17): L9-L19, 2018. doi:10.1088/1361-6560/aa7cd5.
Kyriakou et al., "A review of numberical and experimental compensation techniques for skull-induced phase aberrations in transcranial focused ultrasound", Int J Hyperthermia; 30(1): 36-46, 2014.
Kyriakou et al., "Full-wave acoustic and thermal modeling of transcranial ultrasound investigation of skull-induced aberration correction techniques: a feasibility study", published in Journal of Therapeutic Ultrasound, Jul. 31, 2015; https://www.ncbi.nlm.nih.gov/pmc/articles/PMC4521448/, Chapter "US simulations", "Analytical validation".
Hughes, A et al., "Design of patient-specific-specificlbcused ultrasound arrays for non-invasive brain therapy with Increased trans-skull transmission and steering range", Published online Aug. 3, 2017, available at : https://www.ncbi.nlm.nih.gov/pmc/articles/PMC5727575/.
Lewis, M.A. et al., "Thermometry and Ablation Monitoring with Ultrasound", Mar. 10, 2015, available at: https://www.ncbi.nlm.nih.gov/pmc/articles/PMC4467963/.
International Search Report for PCT CA2020/050731 dated Sep. 22, 2020.
Aarnio J. et al: "A new ultrasound method for determining the acoustic phase shifts caused by the skull bone", Ultrasound in

(56) References Cited

OTHER PUBLICATIONS

Medicine and Biology, New York, NY, US, vol. 31, No. 6, Jun. 1, 2005, pp. 771-780, XP027605464, ISSN: 0301-5629.

* cited by examiner

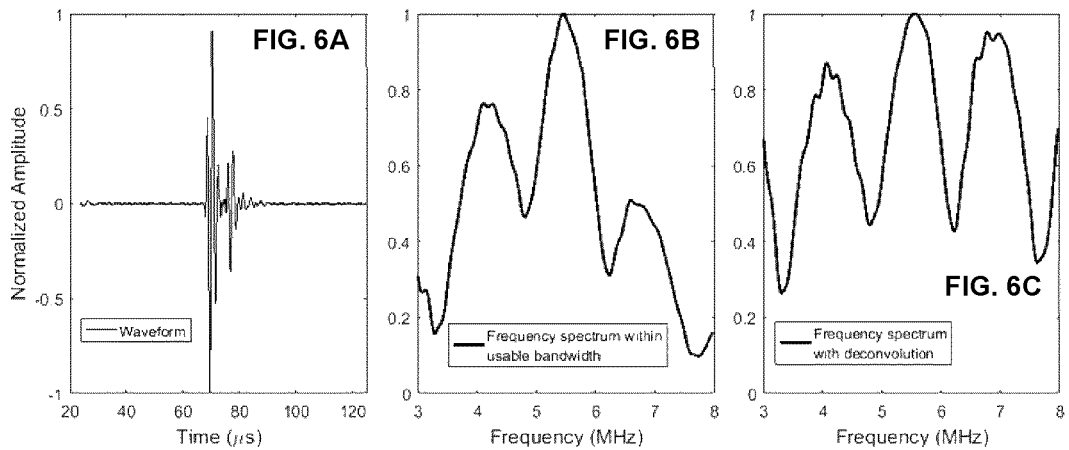
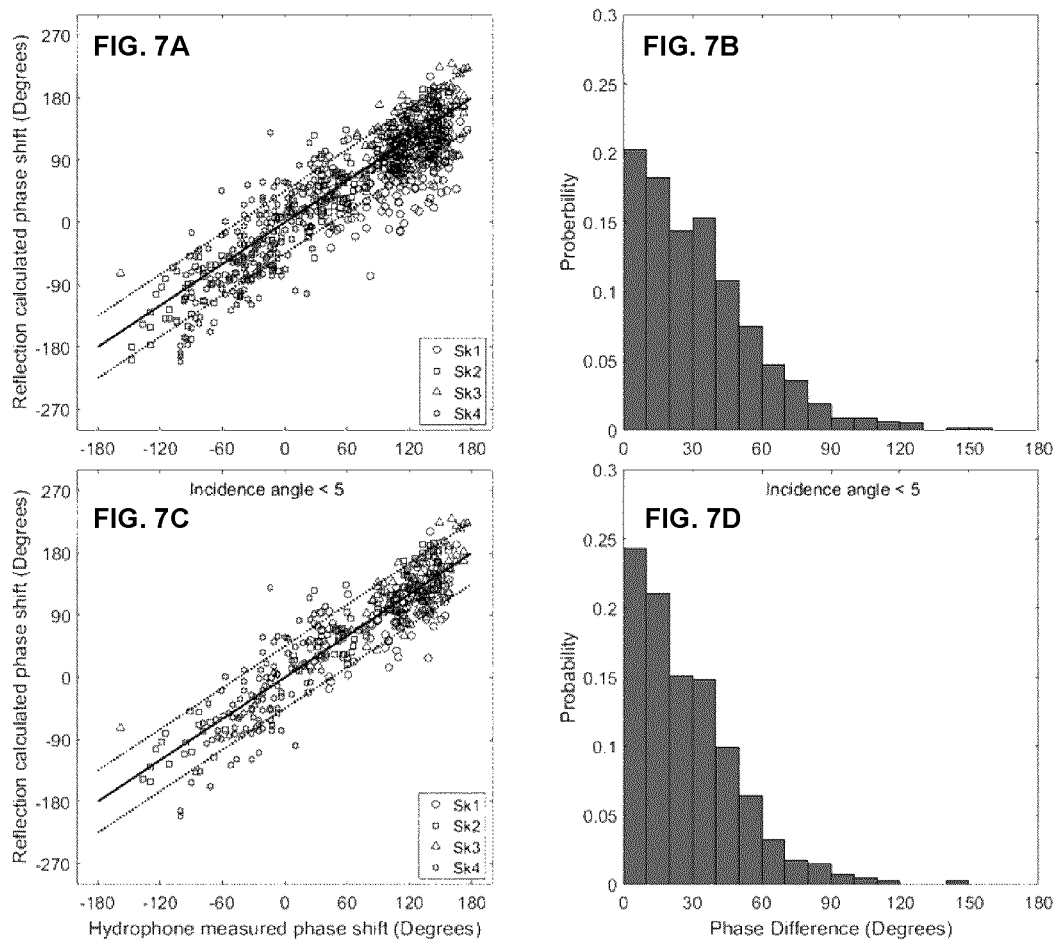

| #Skull | Thickness (mm) | Incident Angle (°) | | Percentage (%) of phase shift difference | | | |
|---|---|---|---|---|---|---|---|
| | | Outer Surface | Inner Surface | < 45° | | < 20° | |
| | | | | Resonance vs Hydrophone | CT-based vs Hydrophone | Resonance vs Hydrophone | CT-based vs Hydrophone |
| Sk1 | 6.7 ± 0.6 | 5.5 ± 3.2 | 7.8 ± 4.5 | 67.4 | 59.1 | 36.2 | 22.8 |
| Sk2 | 7.0 ± 1.5 | 4.5 ± 2.5 | 9.0 ± 5.6 | 86.1 | 76.2 | 45.0 | 31.1 |
| Sk3 | 5.3 ± 0.6 | 5.0 ± 2.8 | 9.1 ± 5.4 | 82.4 | 91.2 | 42.0 | 65.5 |
| Sk4 | 8.5 ± 0.9 | 5.5 ± 3.2 | 9.2 ± 4.4 | 67.9 | 81.8 | 34.5 | 32.5 |
| All 4 skulls | | | | 74.0 | 74.5 | 38.5 | 35.1 |
| All 4 Skulls (incident angle < 5°) | | | | 80.9 | 76.2 | 45.4 | 37.2 |

SYSTEMS AND METHODS FOR REDUCING THERMAL SKULL-INDUCED ABERRATIONS DURING TRANSCRANIAL ULTRASOUND THERAPEUTIC PROCEDURES

CROSS-REFERENCE TO RELATED APPLICATION

This application is a National Phase application claiming the benefit of the international PCT Patent Application No. PCT/CA2020/050731, filed on May 28, 2020 in English, which claims priority to U.S. Provisional Application No. 62/855,283, titled "SYSTEMS AND METHODS FOR REDUCING THERMAL SKULL-INDUCED ABERRATIONS DURING TRANSCRANIAL ULTRASOUND THERAPEUTIC PROCEDURES" and filed on May 31, 2019, the entire contents of which are incorporated herein by reference.

BACKGROUND

The present disclosure relates to ultrasound-based therapy and imaging. More particularly, the present disclosure relates to transcranial ultrasound systems and methods.

Transcranial Focused ultrasound (FUS) therapy has been pursued as a potential alternative to the conventional surgery, as it enables the non-invasive ablation of targets deep in the brain. Currently, this technique has been employed and studied successfully in clinical thermal ablation of small targets for essential tremor (Elias et al. 2013, Lipsman et al. 2013, Elias et al. 2016), brain tumors (McDannold et al. 2010, Coluccia et al. 2014), obsessive-compulsive disorder (Jung et al. 2015), chronic neuropathic pain (Martin et al. 2009, Jeanmonod et al. 2012) and depression (Kim et al. 2018). The essential tremor treatments have now received regulatory approvals from multiple regulatory agencies including U.S. Food and Drug Administration in 2016.

The clinical implementations of transcranial FUS techniques require the capability of accurate and precise targeting through an intact skull, which is challenging due to the inhomogeneity of the skull (Clement and Hynynen 2002a), resulting in a distorted focus in the brain (Fry and Barger 1978). As a result, different approaches have been proposed to correct such aberration. For example, ultrasound imaging time-shift method was used by calculating the time delay corresponding to the peak of the cross-correlation between signals from neighboring transducers (Flax and O'Donnell 1988, O'Donnell and Flax 1988, Nocl, Trahey and Smith 1989). Later, time-reversal mirror was employed by Thomas and Fink (Thomas and Fink 1996) and Tanter et al. (Tenter, Thomas and Fink 1998). In brief, ultrasound was emitted from an implanted transducer in the desired treatment volume. A treatment array was applied to record the waves and re-emit to the target where the transducer was implanted. Meanwhile, a catheter-inserted hydrophone-based correction was proposed for liver (Seip, VanBaren and Ebbini 1994) and for brain (Aubry et al. 2001, Clement and Hynynen 2002b). These methods have shown the feasibility to improve the focusing quality, but an initial invasive implantation of a transducer is required. To achieve a non-invasive transcranial treatment, it was discovered that skull aberration correction can be non-invasively accomplished by using skull density and thickness information obtained from pre-operative CT images (Clement and Hynynen 2002c) that made clinical brain treatments feasible. Several computer models that use the CT information have since been developed and shown to achieve trans-skull focusing (Aubry et al. 2003, Jones, O'Reilly and Hynynen 2015).

Many clinical implementations of transcranial focused ultrasound therapy employ the accurate and precise targeting through an intact skull, which is challenging due to the inhomogeneity of the skull (Clement and Hynynen 2002a), resulting in a distorted focus in the brain (Fry and Barger 1978). As a result, different approaches have been proposed to correct such aberration. For example, ultrasound imaging time-shift method was used by calculating the time delay corresponding to the peak of the cross-correlation between signals from neighboring transducers (Flax and O'Donnell 1988, O'Donnell and Flax 1988, Nocl, Trahey and Smith 1989). Later, time-reversal mirror was employed by Thomas and Fink (Thomas and Fink 1996) and Tanter et al. (Tenter, Thomas and Fink 1998). In brief, ultrasound was emitted from an implanted transducer in the desired treatment volume. A treatment array was applied to record the waves and re-emit to the target where the transducer was implanted. Meanwhile, catheter-inserted hydrophone based correction was proposed for liver (Seip, VanBaren and Ebbini 1994) and for brain (Aubry et al. 2001, Clement and Hynynen 2002b). These methods have shown the feasibility to improve the focusing quality, but an initial invasive implantation of a transducer is required.

To achieve a non-invasive transcranial treatment, it was discovered that skull aberration correction can be non-invasively accomplished by using skull density and thickness information obtained from pre-operative CT images (Clement and Hynynen 2002c) that made clinical brain treatments feasible. Several computer models that use the CT information have since been developed and shown to achieve trans-skull focusing (Aubry et al. 2003, Jones, O'Reilly and Hynynen 2015). The CT information can be also used in the design of acoustic lens with controlled thickness coupled with single element transducer for transcranial applications (e.g. G. Maimbourg, A. Houdouin, T. Deffieux, M. Tanter, and J. F. Aubry, "3D-printed adaptive acoustic lens as a disruptive technology for transcranial ultrasound therapy using single-element transducers," Phys Med Biol, vol. 63, no. 2, p. 025026, Jan. 16, 2018, and G. Maimbourg, A. Houdouin, T. Deffieux, M. Tanter, and J. F. Aubry, "Steering capabilities of an acoustic lens for transcranial therapy: numerical and experimental studies," IEEE Trans Biomed Eng, Mar. 26, 2019).

A method based on the materials' thickness resonance frequencies (Ohkawai 1983, Guyott 1988) had been proposed for the measurements of the phase shifts caused by the skull bones (Aarnio et al. 2005). In the Aarnio study, a wideband ultrasound transducer was used to emit an impulse, and the reflected acoustic signals from the skull inner and outer surfaces were recorded followed by the frequency spectra analysis to extract the resonance frequency of skull bone. In addition, the skull thickness was obtained via direct measurement with caliper or micrometer, which is not available in actual clinical application.

SUMMARY

Various example embodiments of the present disclosure provide systems and methods for the dynamic correction and reduction of thermal variations in skull-induced aberrations during a focused ultrasound therapy procedure. Unlike conventional approaches involving static corrections for skull-induced aberrations, various example embodiments of the present disclosure employ ultrasound detection and a skull thickness estimate from volumetric image data to intermittently and dynamically determine corrections for skull-induced aberrations, such that aberration correction reduction is updated intraoperatively and maintained despite local thermally-induced changes in the speed of sound of the local skull region due to intraoperative intracranial heating. Furthermore, in some example embodiments, a measure dependent on the speed of sound with the skull is intraoperatively determined and compared to a previously determined value of the measure to determine a change in the skull temperature, based on a pre-determined relationship between changes in the measure and changes in skull temperature.

Accordingly, in a first aspect, there is provided a method of intraoperatively reducing skull-induced aberrations during an intracranial focused ultrasound therapy procedure, the method comprising:

after initiating delivery of focused ultrasound to a subject using an array of ultrasound transducers:
a) employing an ultrasound transducer of the array to transmit a non-therapeutic ultrasound pulse and receive a reflected ultrasound pulse, thereby obtaining a receive signal;
b) determining a correction for correcting a therapeutic transmit signal delivered to the ultrasound transducer during subsequent focused ultrasound therapy, wherein the correction is suitable for reducing skull-induced aberrations associated with a local skull region adjacent to the ultrasound transducer, wherein the correction is determined by processing the receive signal and employing a skull thickness estimate associated with the local skull region, and wherein the skull thickness estimate is obtained based on previously measured volumetric image data associated with the subject; and
c) repeating steps a) and b) one or more times during the intracranial focused ultrasound therapy procedure to intermittently recalculate the correction and thereby maintain aberration reduction despite local thermally-induced changes in the speed of sound of the local skull region due to intraoperative intracranial heating.

In another aspect, there is provided a method of intraoperatively reducing skull-induced aberrations during an intracranial focused ultrasound therapy procedure, the method comprising:

after initiating delivery of focused ultrasound to a subject using an array of ultrasound transducers:
a) employing an ultrasound transducer of the array to transmit ultrasound energy and receive reflected ultrasound energy, thereby obtaining a receive signal associated with the reflected ultrasound energy;
b) determining a correction for correcting a therapeutic transmit signal delivered to the ultrasound transducer during subsequent focused ultrasound therapy, wherein the correction is suitable for reducing skull-induced aberrations associated with a local skull region adjacent to the ultrasound transducer, wherein the correction is determined by processing the receive signal and employing a skull thickness estimate associated with the local skull region, and wherein the skull thickness estimate is obtained based on previously measured volumetric image data associated with the subject; and
c) during the subsequent delivery of focused ultrasound to the subject, applying the correction to the therapeutic transmit signal provided to the ultrasound transducer such that skull-induced aberrations are reduced; and
d) repeating steps a)-c) one or more times during the intracranial focused ultrasound therapy procedure to intermittently recalculate the correction and thereby maintain an accuracy of aberration correction despite local thermally-induced changes in the speed of sound of the local skull region due to intraoperative intracranial heating.

In another aspect, there is provided a method of intraoperatively controlling an intracranial ultrasound therapy system for reducing skull-induced aberrations during an intracranial focused ultrasound therapy procedure, the intracranial ultrasound therapy system comprising an array of ultrasound transducers and associated transducer driving circuitry, the method comprising:

after initiating delivery of focused ultrasound to a subject using an array of focused ultrasound transducers:
a) employing an ultrasound transducer of the array to transmit a non-therapeutic ultrasound pulse and receive a reflected ultrasound pulse, thereby obtaining a receive signal;
b) determining a correction for correcting a therapeutic transmit signal delivered to the ultrasound transducer during subsequent focused ultrasound therapy, wherein the correction is suitable for reducing skull-induced aberrations associated with a local skull region adjacent to the ultrasound transducer, wherein the correction is determined by processing the receive signal and employing a skull thickness estimate associated with the local skull region, and wherein the skull thickness estimate is obtained based on previously measured volumetric image data associated with the subject; and
c) controlling the transducer driving circuitry such that the correction is applied to the transmit signal provided to the ultrasound transducer when focused ultrasound therapy is subsequently delivered to the subject during the intracranial focused ultrasound therapy procedure; and
d) repeating steps a)-c) one or more times during the intracranial focused ultrasound therapy procedure to intermittently recalculate the correction and thereby maintain aberration reduction despite local thermally-induced changes in the speed of sound of the local skull region due to intraoperative intracranial heating.

In another aspect, there is provided a method of performing an intracranial focused ultrasound therapy procedure, the method comprising:

delivering focused ultrasound to a subject using an array of ultrasound transducers;
a) employing an ultrasound transducer of the array to transmit ultrasound energy and receive reflected ultrasound energy, thereby obtaining a receive signal associated with the reflected ultrasound energy;
b) determining a correction for correcting a therapeutic transmit signal delivered to the ultrasound transducer during subsequent focused ultrasound therapy, wherein the correction is suitable for reducing skull-induced aberrations associated with a local skull region adjacent to the ultrasound transducer, wherein the correction is determined by processing the receive signal and employing a skull thickness estimate associated with the local skull region, and wherein the skull thickness estimate is obtained based on previously measured volumetric image data associated with the subject; and
c) delivering focused ultrasound therapy to the subject while applying the correction to the therapeutic transmit signal, such that skull-induced aberrations are reduced; and
d) repeating steps a)-c) one or more times during the intracranial focused ultrasound therapy procedure to intermittently recalculate the correction and thereby maintain aberration reduction despite local thermally-induced changes in the speed of sound of the local skull region due to intraoperative intracranial heating.

In another aspect, there is provided a method of measuring a change in skull temperature during an intracranial focused ultrasound therapy procedure, the method comprising:
  a) employing an ultrasound transducer located adjacent to the skull of a subject to transmit a first non-therapeutic ultrasound pulse and receive a first reflected ultrasound pulse, thereby obtaining a first receive signal;
  b) after delivering focused ultrasound to the subject, employing the ultrasound transducer to transmit a second non-therapeutic ultrasound pulse and receive a second reflected ultrasound pulse, thereby obtaining a second receive signal;
  c) processing the first receive signal to determine a first value of a measure dependent on a speed of sound with the skull;
  d) processing the second receive signal to determine a second value of the measure dependent on the speed of sound with the skull; and
  e) employing the first value of the measure, the second value of the measure, and a predetermined calibration between skull temperature and changes in the measure to determine the change in skull temperature.

In another aspect, there is provided an intracranial focused ultrasound therapy system comprising:
  an array of ultrasound transducers;
  transducer driving circuitry operatively coupled to the array of ultrasound transducers; and
  control and processing circuitry operatively coupled to the transducer driving circuitry, the control and processing circuitry comprising at least one processor and associated memory, the memory storing instructions executable by the at least one processor for performing operations comprising:
    after initiating delivery of focused ultrasound to a subject using the array of ultrasound transducers during a focused ultrasound therapy procedure:
    a) employing an ultrasound transducer of the array to transmit a non-therapeutic ultrasound pulse and receive a reflected ultrasound pulse, thereby obtaining a receive signal;
    b) determining a correction for correcting a therapeutic transmit signal delivered to the ultrasound transducer during subsequent focused ultrasound therapy, wherein the correction is suitable for reducing skull-induced aberrations associated with a local skull region adjacent to the ultrasound transducer, wherein the correction is determined by processing the receive signal and employing a skull thickness estimate associated with the local skull region, and wherein the skull thickness estimate is obtained based on previously measured volumetric image data associated with the subject; and
    c) controlling the transducer driving circuitry such that the correction is applied to the transmit signal provided to the ultrasound transducer when focused ultrasound therapy is subsequently delivered to the subject during the intracranial focused ultrasound therapy procedure; and
    d) repeating steps a)-c) one or more times during the intracranial focused ultrasound therapy procedure to intermittently recalculate the correction and thereby maintain aberration reduction despite local thermally-induced changes in the speed of sound of the local skull region due to intraoperative intracranial heating.

In another aspect, there is provided a method of reducing aberrations during an intracranial focused ultrasound therapy procedure, the method comprising:
  employing an ultrasound transducer of the array to transmit a non-therapeutic ultrasound pulse and receive a reflected ultrasound pulse, thereby obtaining a receive signal;
  processing the receive signal to determine that one or more measures associated with the receive signal satisfy exclusion criteria; and
  excluding the ultrasound transducer from use during subsequent delivery of focused ultrasound therapy by the array.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 6A-6C plot (FIG. 6A) measured radiofrequency (RF) signal in time domain; (FIG. 6B) frequency spectrum within the usable bandwidth (0.3-0.8 MHz); and (FIG. 6C) frequency spectrum with deconvolution.

FIG. 7A-7D plot (FIG. 7A) reflection-calculated phase shifts based on resonance method as a function of hydrophone-measured phase shifts; (FIG. 7B) histogram of the phase differences in skull caps Sk1-4; (FIG. 7C) reflection-calculated phase shifts as a function of hydrophone-measured phase shifts; and (FIG. 7D) histogram of the phase differences in skull caps Sk1-4, excluding the measured spots with incident angle 5°. Solid and dotted lines denote 0° and ±45° in phase differences between the two modalities, respectively.

(FIG. 8B) histogram of the phase differences in skull caps Sk1-4; (FIG. 8C) CT-based phase shifts as a function of hydrophone-measured phase shifts; and (FIG. 8D) histogram of the phase differences in skull caps Sk1-4, excluding the measured spots with incident angle 5°. Solid and dotted lines denote 0° and ±45° in phase differences between the two modalities, respectively.

FIGS. 11A-11B plot (FIG. 11A) a summary of the change of phase shift measured on all four skulls with resonance and hydrophone methods and (FIG. 11B) the change of skull resonant frequencies as a function of temperature.

DETAILED DESCRIPTION

Figure 1A:
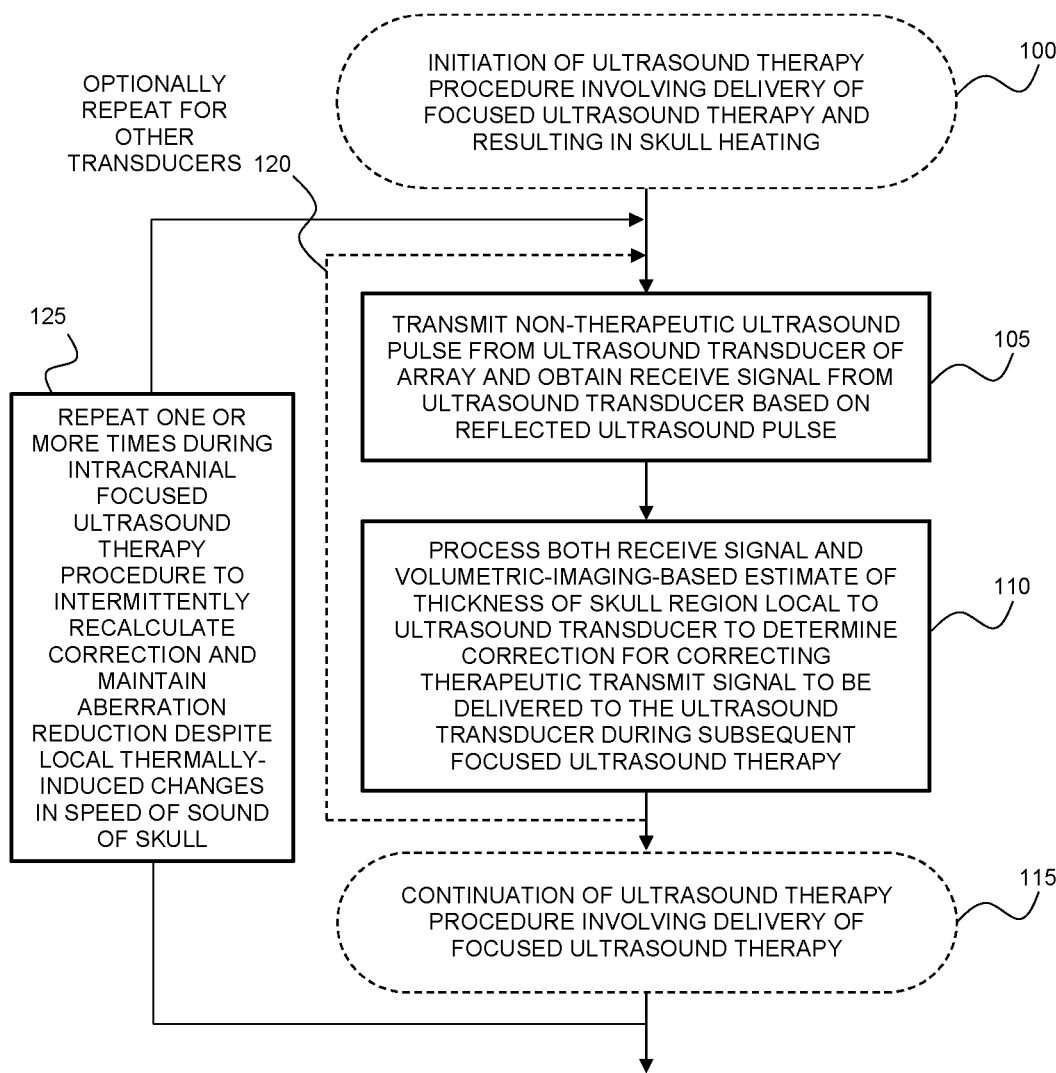
FIG. 1A is a flow chart illustrating an example method of intraoperatively reducing skull-induced aberrations during an intracranial focused ultrasound therapy procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As noted above, several studies previously addressed the need to compensate for skull-induced phase aberrations when performing intracranial focused ultrasound therapy. It was also known (Clement and Hynynen 2002a) that skull-induced phase shifts were substantially insensitive to temperature. Indeed, Clement and Hynynen stated that "phase measurements performed at room temperature may be used for phase correction through a skull at body temperature" and that "temperature rises in the skull bone during a therapeutic treatment (~10° C.) should not significantly change the phase".

The present inventors, after having performed experiments demonstrating a negative correlation between power and acoustic efficiency, and in view of a positive correlation between power and skull heating, suspected that the conclusions previous drawn in the art with regard to the impact of temperature on skull-induced phase aberrations may have been incorrect. Indeed, the present inventors suspected that skull heating resulted in an increase the focal spot size and decrease of heating efficiency of clinical brain treatments as observed in their experiments, and hypothesized that the limiting of focal temperature elevation at higher power may be due to the reduced heating efficiency resulting from focal widening caused by improper correction of a temperature dependence of skull-induced aberration. The present inventors thus suspected that such focal widening may be caused by a failure to compensate for speed of sound changes in the skull resulting from spatially nonuniform increases in skull temperature.

Recognizing this technical problem in the field of intracranial focused ultrasound therapy, the present inventors sought to develop a solution that facilitate the reduction of thermally-induced variations in skull-induced aberrations during focused ultrasound therapeutic procedures.

As explained in the Examples provided below, the present inventors performed a series of experiments that demonstrated that, in stark contrast to the previous teachings and bias provided by Clement and Hynynen 2002a, skull-induced aberrations have a strong dependence on skull temperature. For example, measurements of the skull-induced phase shift with a temperature elevated from 25° C. to 42° C. were performed using both a resonance method and a hydrophone method (described in detail below). The skull-induced phase shift from four example skull samples, measured between room temperature and 42° C. as a function of temperature (at a center frequency of 0.5 MHz) was found to vary significant as a function of temperature, with a dependence on temperature of 2.65° of phase change per degree Celsius. Moreover, the present inventors found that a change of mean resonant frequencies of the measured skulls was inversely proportional to the change in temperature.

The present inventors concluded from these experimental findings that when performing high-intensity transcranial therapeutic ultrasound procedures, a significant temperature rise within skull is expected, contrary to the conventional knowledge in the art, which results in a significant change of skull density and speed of sound, and thus a significant skull-induced phase shift that can impact the efficiency and accuracy of focused ultrasound treatment. It was therefore determined that a method was needed that would facilitate the dynamic, intraoperative, and spatially heterogeneous (transducer-specific) correction of thermally-induced variations in skull-induced aberrations.

Various example embodiments of the present disclosure provide systems and methods for the dynamic correction and reduction of thermal variations in skull-induced aberrations during a focused ultrasound therapy procedure. Unlike conventional approaches in which static corrections for skull-induced aberrations are determined pre-operatively, prior to the commencement of focused ultrasound therapy, and subsequently applied without modification during the procedure, various example embodiments of the present disclosure employ ultrasound detection and the use of a skull thickness estimate from volumetric image data to intermittently and dynamically determine corrections for skull-induced aberrations during a focused ultrasound therapeutic procedure, such that aberration correction reduction is updated intraoperatively and maintained despite local thermally-induced changes in the speed of sound of the local skull region due to intraoperative intracranial heating. Furthermore, in some example embodiments, a measure dependent on the speed of sound with the skull is intraoperatively determined and compared to a previously determined value of the measure to determine a change in the skull temperature, based on a pre-determined relationship between changes in the measure and changes in skull temperature.

In one example embodiment, a method is provided in which ultrasound transducers of a transcranial ultrasound array are employed to intermittently detect ultrasound energy reflected from the skull to noninvasively monitor local skull heating. As explained in detail below, an ultrasound transducer of the transcranial ultrasound array is intermittently employed, during the focused ultrasound therapeutic procedure, to detect reflected ultrasound energy reflected from the local skull region adjacent to the transducer, and the detected signals are processed, and employed in combination with a volumetric-image-based estimate of the local skull thickness, to determine a dynamic correction for adjusting the phases of the driving signals to compensate for the heating induced changes. This dynamic correction may be recomputed intermittently (e.g. periodically or aperiodically) during the focused ultrasound therapy procedure. Moreover, the dynamic corrections may be determined and employed for a plurality of the ultrasound transducers of the array, such as all of the ultrasound transducers of the array.

The example methods and systems described herein may be beneficial in improving the accuracy, efficiency and quality of intracranial focused ultrasound therapeutic procedures. Furthermore, the present example embodiments may improve the feasibility of some intracranial focused ultrasound therapeutic procedures that would have otherwise been deemed unfeasible due to effects of heating. Indeed, although some clinical trials involving intracranial focused ultrasound have been successful, there are many patients for whom it is not possible to reach adequate temperatures for thermal ablation. Moreover, in some cases, focused ultrasound therapy procedures are deemed unfeasible because the skull temperatures would be so high during the procedure that skull damage may be induced. In addition, in some clinical cases, only central targets are treatable due to excessive skull heating. The improved treatment efficiency that may be achieved according to the example embodiments described herein may be effective in reducing the degree of skull heating in such procedures, thereby increasing their potential feasibility.

Referring now to FIG. 1A, an example method is provided a method of intraoperatively reducing skull-induced aberrations during an intracranial focused ultrasound therapy procedure. After initiating delivery of focused ultrasound to a subject using an array of ultrasound transducers (100), an ultrasound transducer of the array is employed to transmit a non-therapeutic ultrasound pulse into a local region of the skull adjacent to the ultrasound transducer and to receive a reflected ultrasound pulse, thereby obtaining a receive signal, as shown at step 105.

The phrase "non-therapeutic", as employed herein, refers to a pulse having an energy less than that that employed by the ultrasound transducer during the delivery of focused ultrasound therapeutic energy, where the non-therapeutic ultrasound pulse is employed to measure reflections of ultrasound energy from the skull as opposed to the delivery of ultrasound energy to an intracranial target for generating a therapeutic effect. The non-therapeutic ultrasound pulse may, in some example embodiments, have a bandwidth that exceeds the bandwidth of the ultrasound pulses employed during focused ultrasound therapy delivery, such that the reflected signal can be processed to accurately determine resonant features in the frequency spectrum of the reflected pulse and/or determine a transit time of the reflected pulse. In some example embodiments, the non-therapeutic ultrasound pulse, which may alternatively be referred to as a "diagnostic" ultrasound pulse, may have a bandwidth of at least 500 kHz. In some example implementations, the center frequency of the non-therapeutic ultrasound pulse may range between 0.5 MHz and 15 MHz.

The receive signal is then processed, as shown at 110, along with an estimate of the local skull thickness that is obtained from the processing of volumetric image data associated with the subject, to determine a correction for correcting a therapeutic transmit signal delivered to the ultrasound transducer during subsequent focused ultrasound therapy.

The correction is calculated such that it is suitable for reducing or substantially eliminating skull-induced aberrations associated with the local skull region adjacent to the ultrasound transducer. For example, the correction may be a phase correction that is employed to adjust the phase of the transmit signal delivered to the ultrasound signal during the subsequent delivery of focused ultrasound energy. In another example embodiment, the correction may be a time delay that is employed to delay the delivery of the transmit signal. Various non-limiting examples of a suitable correction and its application are described in further detail below.

As shown at 120 in FIG. 1A, steps 105 and 110 may be repeated for one or more ultrasound transducers of the array. In one example implementation, corrections are computed for all of the ultrasound transducers of the array. In another example implementation, corrections may computed for a subset of the ultrasound transducers of the array.

These steps may then be repeated one or more times during the intracranial focused ultrasound therapy procedure (115), as shown at 125, to intermittently recalculate the correction(s) and thereby maintain aberration reduction despite local thermally-induced changes in the speed of sound of the local skull region due to intraoperative intracranial heating. While FIG. 1A shows corrections being computed after the initiation of focused ultrasound therapy (100), it will be understood that FIG. 1A is not intended to be limiting and that corrections may be computed prior to the initiation of focused ultrasound therapy (e.g. an initial correction may be computed for use during the initial phase of focused ultrasound therapy prior to appreciable skull heating).

A non-limiting example of the calculation of a correction for a given ultrasound transducer is provided below. According to the present example, a correction may be computed by first processing the receive signal obtained from the detected reflection of the ultrasound pulse, where the processing is performed in the frequency domain to identify resonances associated with the local skull region adjacent to the ultrasound transducer.

The frequency spectrum of the reflected signal from a broadband pulse in a lossy medium yields a result similar to the intensity-transmission coefficient:

$$T = \frac{1}{1 + \frac{1}{4}\left[\frac{(\rho c)_b}{(\rho c)_w} - \frac{(\rho c)_w}{(\rho c)_b}\right]^2 \sin^2 k_b d}, \quad (1)$$

where $\rho$, c, $k_b$, and d represent the density, speed of sound (SoS), wave number and thickness, respectively, and the subscript b and w denote the propagating medium bone and water, respectively. From Eqn. (1), it is evident that at frequencies such that $k_b d$=n$\pi$, total transmission occurs, which is shown as a decreased reflection from skull bone on the frequency spectra of the reflected signal. These frequency minima are the resonant frequencies of the bone layer and can be obtained by locating the zeros of the first derivatives with respect to frequency:

$$f_i = n\frac{c_b}{2d}. \quad (2)$$

From Eqn. (2), the SoS in bone can be calculated as $$C_b = 2d(f_{i+1} - f_i) = 2d\Delta f. \quad (3)$$

The time delay caused by the skull insertion can be represented as $$t = \frac{d}{c_b} - \frac{d}{c_w} = \frac{1}{2\Delta f} - \frac{d}{c_w}, \quad (4)$$

which yields to the equation of phase difference caused by the skull:

$$\Delta\phi = 2\pi f t = 2\pi f\left(\frac{1}{2\Delta f} - \frac{d}{c_w}\right). \quad (5)$$

where f represents the center frequency of the transducer, the SoS in the water $c_w$ is temperature dependent, and d is the thickness of the skull bone at the targeted spots, which may be obtained from volumetric image data associated with the subject (such as pre-operative computed tomography images), as described further below.

After the signals reflected (echoed) from the skull surfaces are recorded, a Fourier transform may be applied followed by a deconvolution of the transducer's impulse response. Resonant features in the frequency spectrum may then be employed to calculate the phase shift. In the Examples provided below, the local minima within the bandwidth of the transducer (0.3-0.8 MHz) were used to calculate the phase shift and an average was taken at each spot. The results were compared to the gold-standard hydrophone method, in which the waveforms were digitally filtered with a fourth order Butterworth bandpass filter (0.1-1 MHz) and the change in the time of flight was calculated through cross-correlating the data with and without the skull.

The local thickness of the skull may be calculated from the volumetric image data, such as computed tomography (CT) or magnetic resonance imaging (MRI). An example method of calculating the local skull thickness using pre-operative CT image data is provided in the Examples section below.

The volumetric image data may be transformed from the reference frame of the volumetric imaging system to the intraoperative reference frame by applying a suitable transformation in order to facilitate the determination of a skull thickness estimate that is valid for the local skull region adjacent to the ultrasound transducer. For example, skull registration can be achieved via an ultrasound-based method as described in O'Reilly, et al., 2016). Briefly, the transducers are excited one at a time with a single cycle burst. The reflected signals from the skull outer surface are recorded and the first echoes are used to calculate the distance to the points on the skull from the time of flight. The outer surface of the skull is segmented from the CT data and defined by a series of vertices and faces. Given the CT and ultrasound data, the skull positions can then be solved using a closest-points based approach (e.g. Besl and McKay, 1992) and registration can be determined.

While the present example embodiment involved the calculation of a phase change correction, it will be understood that the correction could alternatively be computed according to another metric, such as a time delay.

Furthermore, while the preceding example implementation involved the calculation of the correction based on an analysis of resonant features in the frequency spectrum of the receive signal, it will be understood that other methods of processing the receive signal may be employed in the alternative, when determining the correction.

For example, in one alternative example implementation, a time domain analysis may be performed using a pulse-echo analysis method. Denoting the time of arrival of the 1st and the 2nd echoes as t1 and t2, respectively, the time delay for propagation through the local skull region can be represented as $\Delta t = (t2-t1)/2$, resulting in a phase shift. This time delay is the net time delay for the propagation through the skull. A time shift correction resulting from the perturbation to $\Delta t$ that is caused by the presence of bone instead of water (the time delay from skull insertion) may then be calculated as $\Delta t_{pulse-echo} = d/c_b$, so the time delay from skull insertion is $t = d/c_b - d/c_w = \Delta t_{pulse-echo} - d/c_w$, which can be calculated using the local skull thickness estimate d from processing of the volumetric image data. It will be understood that the time domain method should be performed using a non-therapeutic ultrasound pulse having a duration that is less than the time of flight for a round trip within the skull.

It will be understood that the ultrasound transducers of the array may be single or multi-element ultrasound transducers, such as a single focused transducer element or a phased array. In some example implementations, the ultrasound transducers may be configured to achieve a focus within the skull (examples of such a configuration are provided below).

As explained in the Examples section below, the present inventors have found that the present example correction methods achieve superior performance when the ultrasound transducers of the array are positioned such that their respective beam axes are normal to the skull surface. Such alignment may be achieved, for example, using a phased array configuration of the ultrasound element and electronic beam steering, such that normal incidence is achieved when the summation of the peak value in the reflected signals received by each element in the phase array reaches maximum. In an alternative example implementation, the angle of a single element transducer may be changed until the maximum echo from the skull surface is received. The changing of the angle of the transducer could be performed, for example, mechanically (using a single element transducer) or electronically (using a phased array transducer).

In some example embodiments, the receive signal may be employed to identify one or more outlier transducers of the array and to exclude the one or more outlier transducers from use during focused ultrasound therapy, in order to avoid the use of specific ultrasound transducers that are likely to impair the ability to achieve an accurate intracranial focus. For example, exclusion criteria may be developed that, if satisfied by one or more measures obtained by processing the receive signal of a given ultrasound transducer, would exclude the given transducer from inclusion during subsequent focused ultrasound therapy. The measurement of the receive signal and the assessment of the whether or not the one or more measures satisfy the exclusion criteria, may be performed prior to initiating delivery of focused ultrasound therapy or after initiating focused ultrasound therapy.

In one example implementation, the exclusion criteria may involve a comparison of one or more measures associated with a signal-to-noise ratio (SNR) of the frequency spectra to pre-established thresholds. In another example implementation, if the frequency spectrum obtained from a given ultrasound transducer of the array includes multiple spikes satisfying pre-determined criteria (e.g. spike width and height; and/or spike quantity), which are signs of shear wave propagation due to large incidence angles, the given ultrasound transducer may be excluded. Another example of exclusion criteria could involve a comparison of a measured incidence angle, which can be measured, for example, by firstly finding the centroid of a triangular mesh, which is on the registered meshed skull outer surface segmented from CT, with shortest distance to every point along the discretized incident ray pointing from the transducer center to the target, and then calculating the angle between the incident ray and the normal of the triangular surface on the skull of a given ultrasound transducer to pre-determined a threshold, excluding ultrasound transducers that exceed a pre-determined maximum incident angle.

In other example implementations, the exclusion criteria may be assessed based on a comparison of the receive signal with other receive signals. In one example implementation, the receive signal of a given ultrasound transducer may be compared with receive signals obtained from other nearby ultrasound transducers (e.g. adjacent ultrasound transducers or ultrasound transducers within a pre-determined distance from the given ultrasound transducer) to assess whether or not the receive signal from the given ultrasound transducer fails to satisfy similarity criteria. In other example implementations, the ultrasound beam of the given ultrasound transducer may be scanned (e.g. electrically or mechanically scanning the beam) within a skull region proximal to the ultrasound transducer, and multiple receive signals obtained while scanning the skull region may be compared when assessing exclusion criteria. In such cases, the ultrasound transducer may be excluded if inconsistent frequency spectra are detected among multiple receive signals (e.g. if comparative measures obtained by processing multiple receive signals fail to satisfy pre-determined similarity criteria). It will be understood that the preceding example embodiments involving the exclusion of one or more ultrasound transducers based on the assessment of criteria may be performed in the absence of determining dynamic corrections that compensate for thermally induced changes in skull-induced aberration.

In one example embodiment, a correction for correcting a transmit signal delivered to a given ultrasound transducer of the array may be determined, at least in part, based on respective corrections determined for one or more ultrasound transducers residing adjacent to the given ultrasound transducer.

In some example implementations, it may beneficial for the skull thickness and incidence angle calculation to be based on multiple paths in the processing of the volumetric image data. If it is determined that the skull thickness (or another measure) varies beyond a pre-determined threshold, the location within the skull may be excluded during the initial design of the array. It is noted that volumetric image data (e.g. a CT scan) a high resolution (e.g. a resolution exceeding 0.082 mm/pixel (Treece et al. 2010)) will provide a clearer boundary of the cortical bones and lead to a better fitting result with the thickness calculation.

In some example embodiments, the receive signal may be processed to enable an intraoperative determination of changes in the temperature of the skull. As shown in the Examples section below, the present inventors determined that changes of the resonant frequency of the skull have a linear relationship with temperature (see, for example, FIG. 11B). Accordingly, a relationship between the resonant frequency, or one or more other measures obtained from the receive signal that are dependent on the speed of sound in a skull (not necessarily the skull of the subject, e.g. an average relationship based on measurements from multiple skulls), and temperature, may initially be determined or obtained, as shown in 150 in FIG. 1B. As shown at steps 155 and 160, a non-therapeutic ultrasound pulse may be delivered to a subject by an ultrasound transducer of the array, and an initial value of a measure dependent on the speed of sound in the skull may be determined by processing the receive signal obtained from the detection of ultrasound energy reflected from the local skull region associated with the ultrasound transducer. After the delivery of focused ultrasound energy (165), an updated value of the measure may be determined, as shown at steps 170 and 175. The relationship obtained in step 150 may then be employed to determine, based on the change in the measure relative to its previous value, a change in the temperature within the local skull region associated with the ultrasound transducer, as shown at step 180. The process may be repeated, as shown at 190, one or more times to intermittently and intraoperatively track changes in the local temperature of the skull.

Figure 1B:
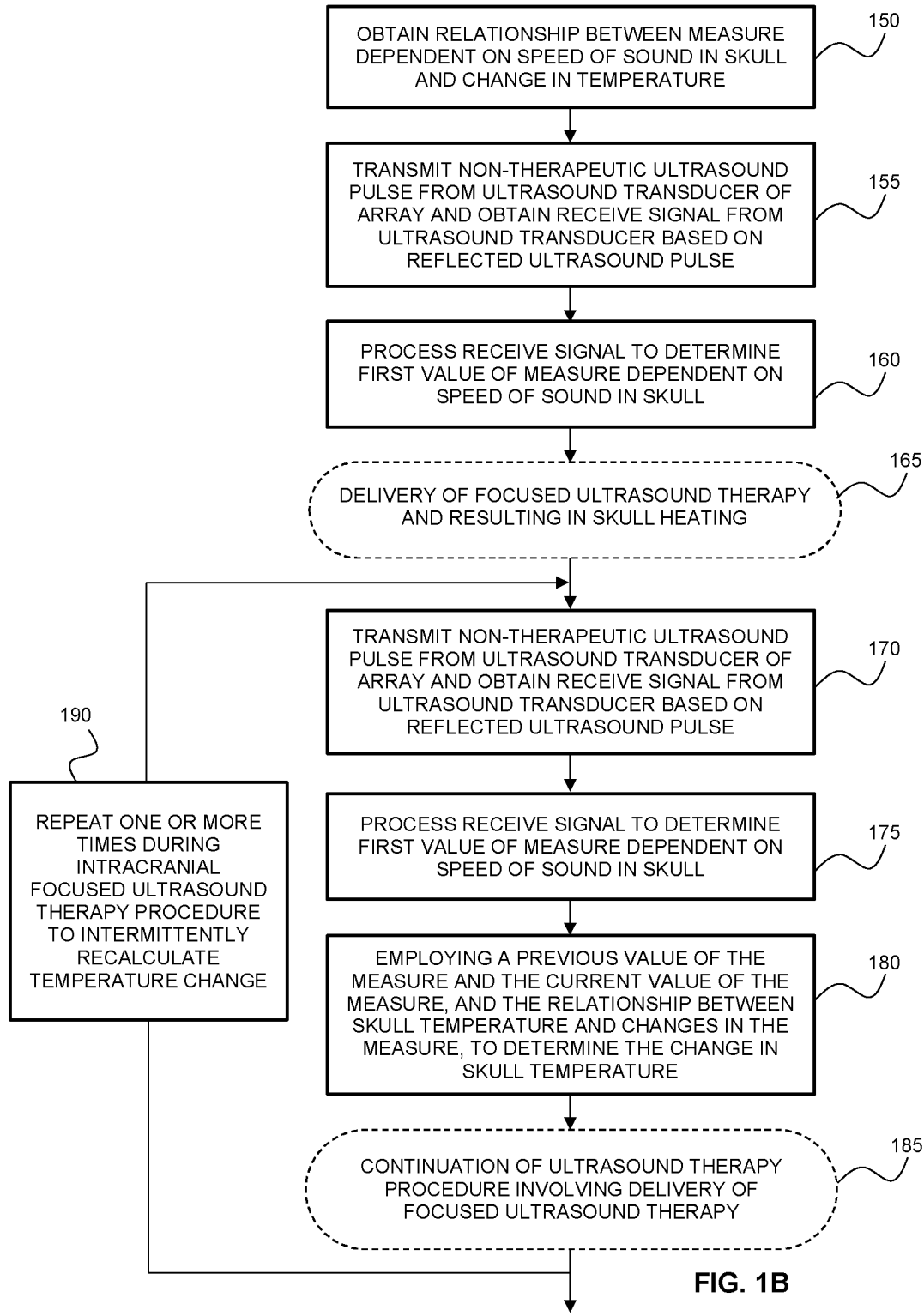
FIG. 1B is a flow chart illustrating an example method of intraoperatively tracking changes in skull temperature during an intracranial focused ultrasound therapy procedure.

Although not shown in FIG. 1B, this process may be performed for one or more additional ultrasound transducers. For example, when performed for a substantial number of the ultrasound transducers of the array, such as at least half of the transducers, the measurements may be employed to generate an (optionally dynamic) heat map of the skull. It will be understood that the method in FIG. 1B may be implemented such that the initial determination of the measure dependent on the speed of sound may be performed prior to the initiation of focused ultrasound therapy (thereby permitting the tracking of temperature changes relative to the skull temperature before therapy), or after initiation of focused ultrasound therapy.

Figure 2:
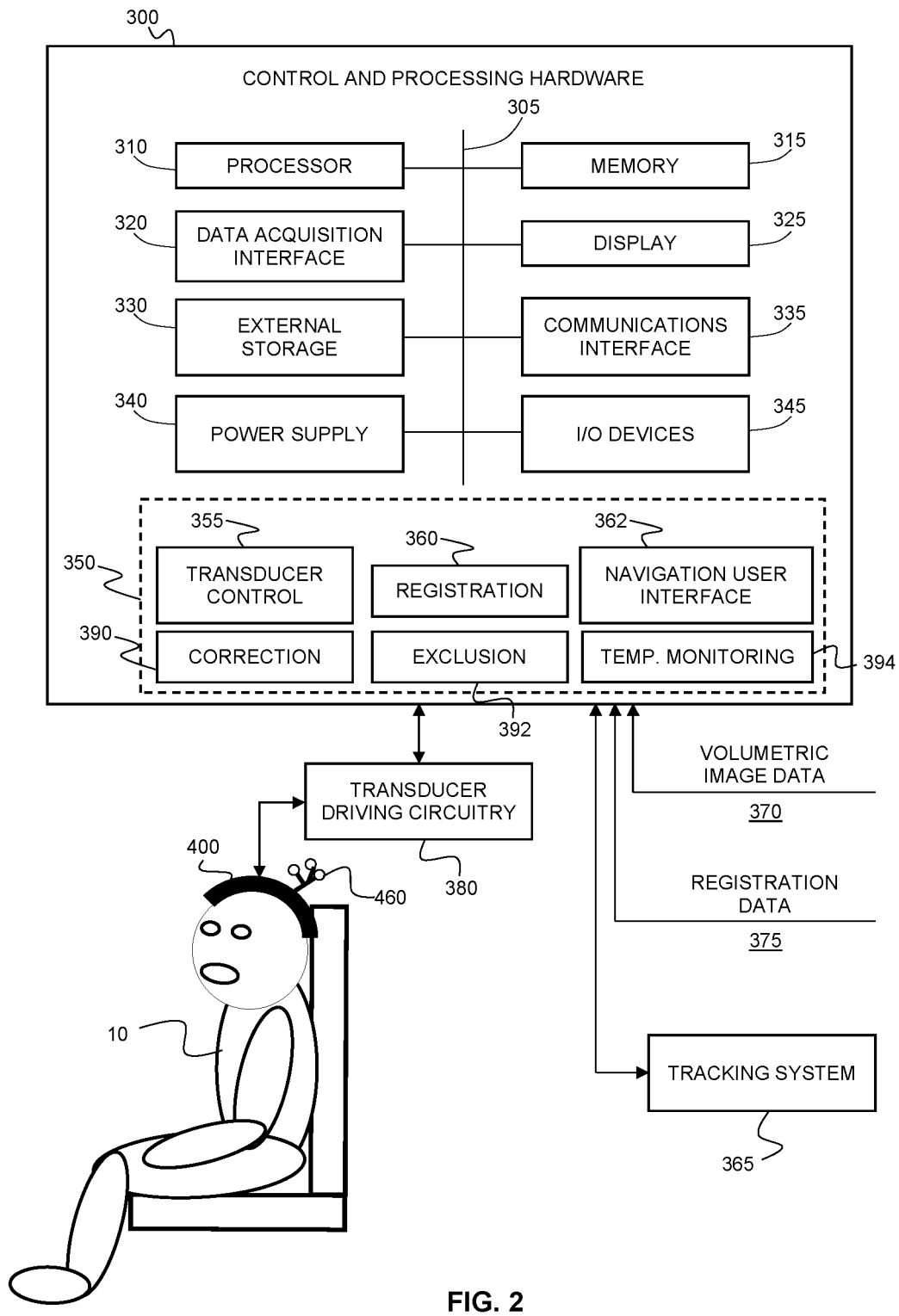
FIG. 2 shows an example system for performing transcranial diagnostic and/or therapeutic procedures.

FIG. 2 provides a block diagram illustrating an example implementation of a system for performing diagnostic or therapeutic transcranial procedures. Control and processing hardware 300 is operably connected to the transcranial headset 100, optionally via transducer driver electronics/circuitry 380.

The control and processing hardware 300, which includes one or more processors 310 (for example, a CPU/microprocessor), bus 305, memory 315, which may include random access memory (RAM) and/or read only memory (ROM), a data acquisition interface 320, a display 325, external storage 330, one more communications interfaces 335, a power supply 340, and one or more input/output devices and/or interfaces 345 (e.g. a speaker, a user input device, such as a keyboard, a keypad, a mouse, a position tracked stylus, a position tracked probe, a foot switch, and/or a microphone for capturing speech commands).

Volumetric image data 370 and transducer registration data 375 may be stored on an external database or stored in memory 315 or storage 330 of control and processing hardware 300.

The tracking system 365 may optionally be employed to track the position and orientation of the patient, via detection of one or more fiducial markers 460 attached to the transcranial headset 400, and optionally one or more medical instruments or devices also having fiducial markers attached thereto. For example, passive or active signals emitted from the fiducial markers may be detected by a stereographic tracking system employing two tracking cameras. The transducer driving electronics/circuitry 380 may include, for example, but is not limited to, Tx/Rx switches, transmit and/or receive beamformers.

The control and processing hardware 300 may be programmed with programs, subroutines, applications or modules 350, which include executable instructions, which when executed by the one or more processors 310, causes the system to perform one or more methods described in the present disclosure. Such instructions may be stored, for example, in memory 315 and/or other storage.

In the example embodiment shown, the transducer control module 355 includes executable instructions for controlling the transducers of the transcranial headset 400 to deliver energy to a target location or region of interest, based on the registration of the transducer positions and orientations with the volumetric image data as per the transducer registration data 375. For example, the transcranial headset 400 may support a plurality of phased-array transducers, and transducer control module 355 may control the beamforming applied (on transmit and/or receive) to deliver, based on the known positions and orientations of the phased array transducers relative to the volumetric image data, one or more focused energy beams to a region of interest in the far field regions of the transcranial ultrasound transducer array elements. The region of interest may be specified intraoperatively by a user (e.g. via a user interface controlled by control and processing hardware 300) or according to a pre-established surgical plan.

The registration module 360 may optionally be employed for registering volumetric image data 370 to an intraoperative reference frame associated with tracking system 365. The optional guidance user interface module 362 includes executable instructions for displaying a user interface showing spatially registered volumetric images for image-guided procedures. The registration module 360 may also intraoperatively receive spatial correction information based on a detected spatial offset between the transcranial frame and the patient's head (which may be provided by a subset of distance-sensing transducers) and employ this spatial correction information to dynamically adjust (e.g. correct) the registration between the transducers and the volumetric image data.

The correction module 390 includes executable instructions to perform, for example, the method illustrated in FIG. 1A for determining intraoperative corrections that compensate for thermally-induced changes in skull-induced aberrations, via control of the transducer driving circuitry 380. The exclusion module 392 includes executable instructions for identifying one or more ultrasound transducers that satisfy exclusion criteria, for example, as per the methods described above. The temperature monitoring module 394 includes executable instructions to perform, for example, the method illustrated in FIG. 1A for the intraoperative tracking of local skull temperature changes, via control of the transducer driving circuitry 380.

Although only one of each component is illustrated in FIG. 2, any number of each component can be included in the control and processing hardware 300. For example, a computer typically contains a number of different data storage media. Furthermore, although bus 305 is depicted as a single connection between all of the components, it will be appreciated that the bus 305 may represent one or more circuits, devices or communication channels which link two or more of the components. For example, in personal computers, bus 305 often includes or is a motherboard. Control and processing hardware 300 may include many more or less components than those shown.

The control and processing hardware 300 may be implemented as one or more physical devices that are coupled to processor 310 through one of more communications channels or interfaces. For example, control and processing hardware 300 can be implemented using application specific integrated circuits (ASICs). Alternatively, control and processing hardware 300 can be implemented as a combination of hardware and software, where the software is loaded into the processor from the memory or over a network connection.

Some aspects of the present disclosure can be embodied, at least in part, in software, which, when executed on a computing system, transforms a computing system into a specialty-purpose computing system that is capable of performing the methods disclosed herein. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Figure 3A:
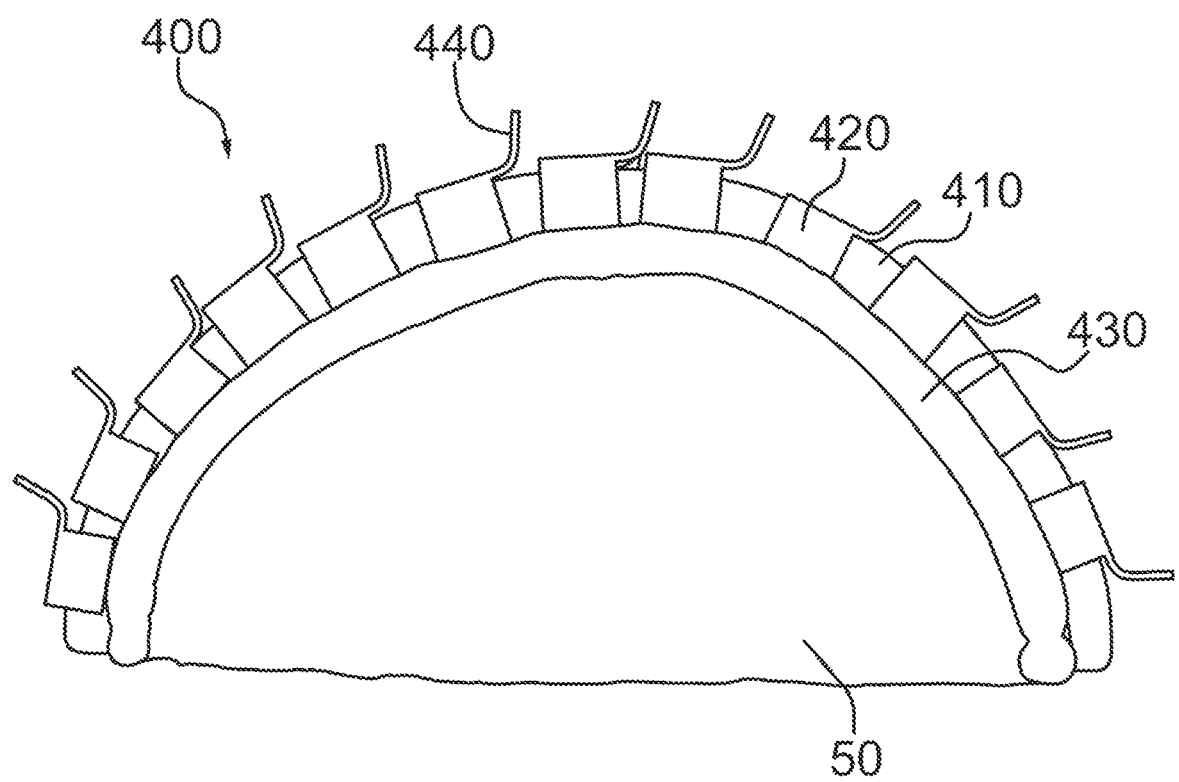
FIG. 3A illustrates a cross-sectional illustration of an example patient-specific headset for performing transcranial therapeutic procedures.

Referring now to FIG. 3A, a non-limiting and example patient-specific headset 400 for performing transcranial diagnostic or therapeutic procedures is shown worn on the head 50 of a patient. The patient-specific headset 400, which includes a patient-specific frame (support structure) 410 that supports a plurality of transducers 420, conforms to the anatomical contour of at least a portion of the patient's head. The patient-specific frame 410, which is shown in cross-section in FIG. 3A, mechanically supports transducers 420 in pre-selected positions and orientations. The transducers 420 may be used to transmit and/or receive energy for brain diagnostic or therapeutic purposes or for localization of the skull surface.

The patient-specific frame 410 includes a plurality of attachment interfaces for receiving and supporting the transducers 420. In the example embodiment shown in FIG. 3A, the attachment interfaces are provided as apertures (recesses) into which the transducers 420 are placed. The transducers 420 may be affixed to the patient-specific frame 410 according to a wide variety of different means, such as, but not limited to, with an attachment mechanism (e.g. via fasteners that extend into the patient-specific frame 410, optionally into pre-formed holes), or an adhesive such as a glue. In the example implementation shown in FIG. 3A, the transducers 420 are remotely interfaced with electronics through wires or through a flexible printed circuit board 440. The transducers 420 may be removably attachable to the patient-specific frame 410.

The example patient-specific headset shown in FIG. 3A may also include a coupling layer 430 that is provided adjacent to an inner surface of the patient-specific frame. The outer surface of the coupling layer 430 contacts distal surfaces of the transducers 420, and the inner surface of the coupling layer contacts the patient's head 50, thereby facilitating coupling of energy between the transducers in the patient-specific frame and the patient's head. The inclusion of the coupling layer 430, and the composition and/or geometry of the coupling layer, may be dependent on the type of transducers 420. For example, if the transducers 420 are ultrasound transducers, the coupling layer 430 may be an acoustic coupling layer that facilitates propagation of acoustic waves and reduces reflections at interfaces. In one example implementation, the coupling layer 430 includes an elastic membrane that retains a liquid layer between the transducer surfaces and the elastic membrane, such that coupling to the skin is achieved.

Figure 3B:
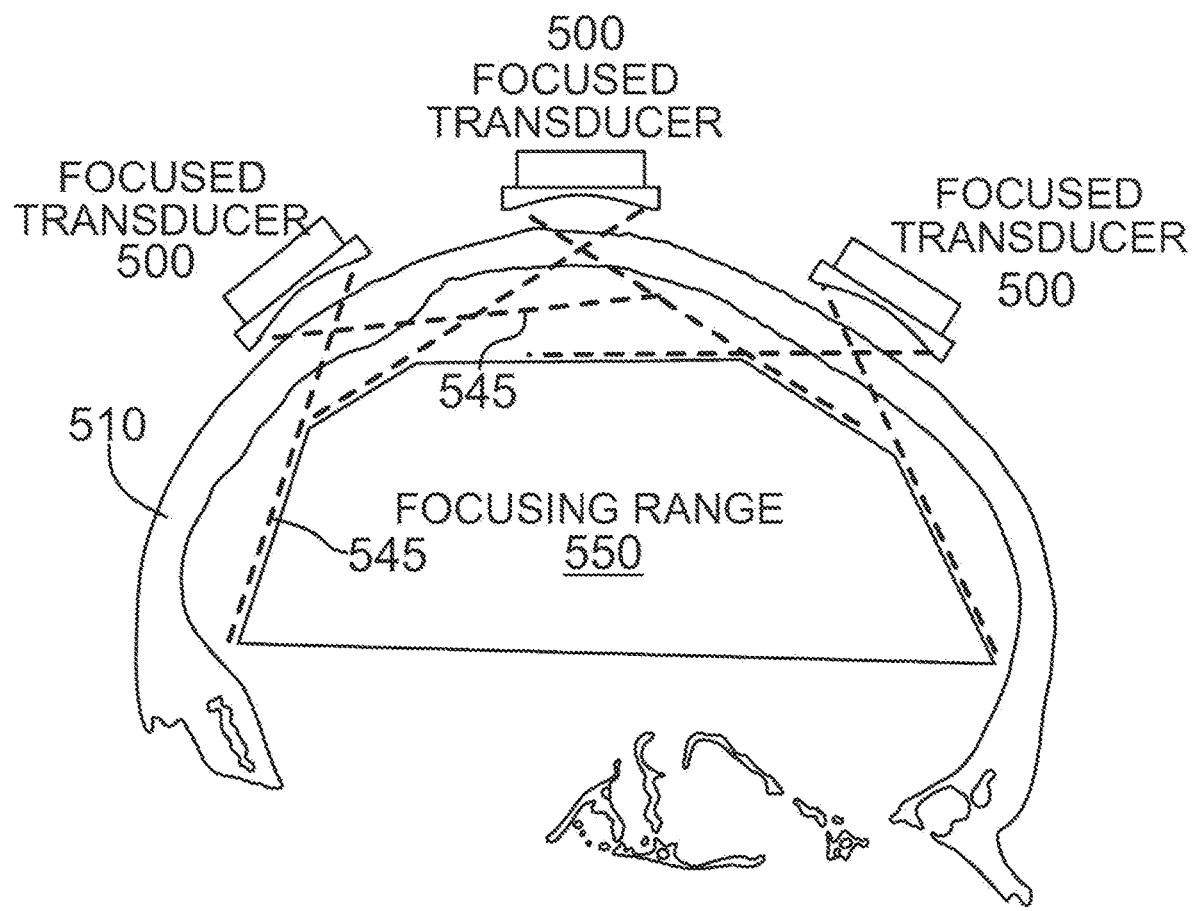
FIG. 3B illustrates an example embodiment in which transcranial ultrasound transducer array elements are supported relative to the skull by a support frame, where the ultrasound beams from the transcranial ultrasound transducer array elements are emitted such they are individually defocused in the far field, while overlapping in the far field to generate a focus.

Some transcranial ultrasound arrays have met with challenges in achieving off-center target sonications (e.g. targets that are more than 2-4 cm away from the center of the brain) due to the high acoustic impedance of the skull, which prohibits the transmission of longitudinal waves at oblique angles and confines therapeutic procedures to targets within a central region of the brain. Referring now to FIG. 3B, an example illustration of a transcranial ultrasound transducer array is shown that addresses this problem by providing an array configured to achieve high levels of beam steering through the skull. This is achieved by positioning the transcranial ultrasound transducer array elements relative to the skull such that the far field of each ultrasound beam lies within the brain and controlling the timing of ultrasound pulses emitted by each transducer array element such that the pulses arrive in-phase at the desired target.

The example transcranial ultrasound transducer array shown in FIG. 3B includes a plurality of transcranial ultrasound transducer array elements 500, which are supported relative to the head of the subject by a frame (not shown). Each transcranial ultrasound transducer array element emits a respective focused ultrasound beam, shown by the dashed lines. Although the illustration in FIG. 3B shows only three transducers for illustrative purposes, a transcranial device will preferably include many more than three elements in order to achieve suitable focusing, as described further below.

As illustrated in the example embodiment shown in FIG. 3B, each transcranial ultrasound transducer array element 500 is positioned such that its respective focus lies within the skull. This is more clearly shown in FIG. 3C, which shows the focusing of a single transcranial ultrasound transducer array element 500 (shown as comprising an active transducer portion 502 and an optional backing 504) to a focal region 520 within the skull 510. By focusing the ultrasound beams within the skull, the near field region 530 of each beam is localized within or near the skull, with the result that the portion of the beam that extends within the brain is in the far field. This is shown in FIG. 3B, where the transcranial ultrasound transducer array elements 500 are focused such that their respective ultrasound beams are diverging (shown by cone 545) within the brain, propagating within the far field. In contrast to other forms of transcranial ultrasound, the individual foci of the transcranial ultrasound transducer array elements are spatially separated, and the ultrasound beams of the transcranial ultrasound transducer array elements overlap in their respective far fields.

As shown in FIG. 3B, the transcranial ultrasound transducer array elements 500 may be oriented such that their respective ultrasound beams enter the skull at normal incidence, or at approximately normal incidence (e.g. within ±15°). In other example implementations, the ultrasound beams may be directed toward the skull within ±10°, within ±5°, or within ±2° of normal incidence. By orienting the transcranial ultrasound transducer array elements 500 in this manner, and focusing their ultrasound beams within or near the skull, the respective ultrasound beams propagate within the skull as plane waves, and thereby enter the brain with reduced loss from impedance mismatches due to bone and tissue, and due to bone and water.

Furthermore, by orienting the transcranial ultrasound transducer array elements 500 at or near normal incidence and focusing the ultrasound beams within or near the skull, each ultrasound beam probes a small region of the skull and is thus less likely to be susceptible to the effects of inhomogeneities within the skull that can cause scattering due to local impedance mismatch and propagating effects due to local changes in the speed of sound. In other words, the propagation of each ultrasound beam through a small area of the skull having less variability in the skull density and in other properties allows for improved correction for the bone induced effects on the wave propagation.

Figure 3C:
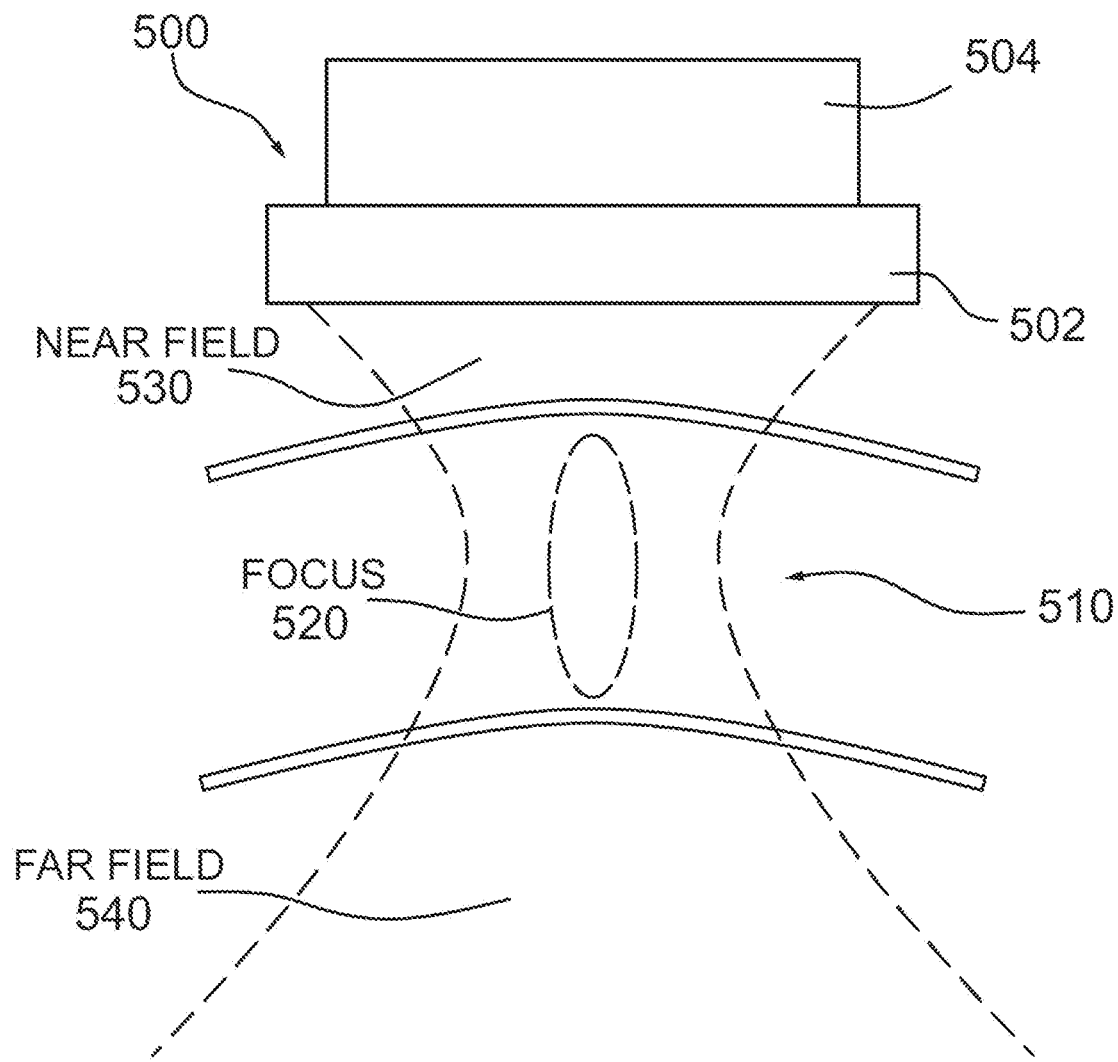
FIG. 3C illustrates an example embodiment showing the positioning and focusing of a transcranial ultrasound transducer array element relative to the skull, such that the focus of the transcranial ultrasound transducer array element lies within the skull.
Figure 3D:
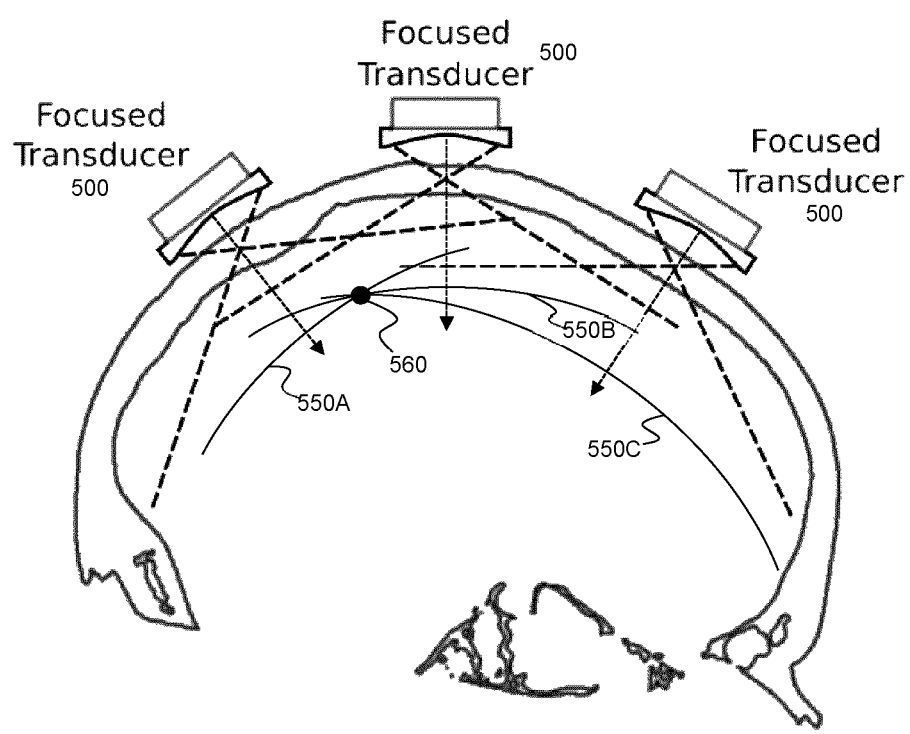
FIG. 3D illustrates the focusing of wavefronts from multiple transcranial ultrasound transducer array elements in the far field.

Referring now to FIG. 3D, the timing of the pulses (and/or phase) emitted by each transcranial ultrasound transducer array element 500 is controlled in order to generate constructive interference at or within a target region residing within the brain. In other words, by supporting a sufficient number of transcranial ultrasound transducer array elements 500 around the head, the energy from the transcranial ultrasound transducer array elements 500 can be focused into a desired target location within the brain by adjusting the phase of the ultrasound waves generated by the transcranial ultrasound transducer array elements 500 or by adjusting the timing if short bursts are transmitted by the transcranial ultrasound transducer array elements 500. This is illustrated in FIG. 3D in the case of short bursts of ultrasound waves, where the timing of the emitted pulses are controlled such that their wave fronts 550A, 550B and 550C are spatially and temporally aligned at focus 560.

As shown in FIG. 3B, each of the transcranial ultrasound transducer array elements 500 may be oriented such that all of their far field regions spatially overlap within a least a portion of the brain (shown as focusing range or focusing region 550), thereby allowing for far-field focusing within this region via control of timing of the emission of ultrasound energy from the transcranial ultrasound transducer array elements 500 (e.g. operating the transcranial ultrasound transducer array as a phased array). In some example embodiments, the focusing region 550 may lie within a portion of the brain that is known to contain a target for therapy or imaging, such as a known or suspected tumor, such that the far-field regions overlap at the target region, but need not overlap elsewhere in the brain.

Although the transcranial ultrasound transducer array elements shown in FIGS. 3B-3D are illustrated as fixed-focus concave transducers, it will be understood that one or more (e.g. all) of the transcranial ultrasound transducer array elements 500 may be phased-array transducers, henceforth referred to as a sub-array. The term "sub-array" is employed herein to clearly distinguish array elements of the transcranial ultrasound transducer array from elements of a phased array transducer that is employed as a transcranial ultrasound transducer array element of the transcranial ultrasound transducer array. The use of a phased sub-array for a transcranial ultrasound transducer array element may be beneficial in that it permits the selection of, and/or adjustment of, the focal point of the transcranial ultrasound transducer array element, without requiring mechanical repositioning of the transcranial ultrasound transducer array element.

Figure 4A:
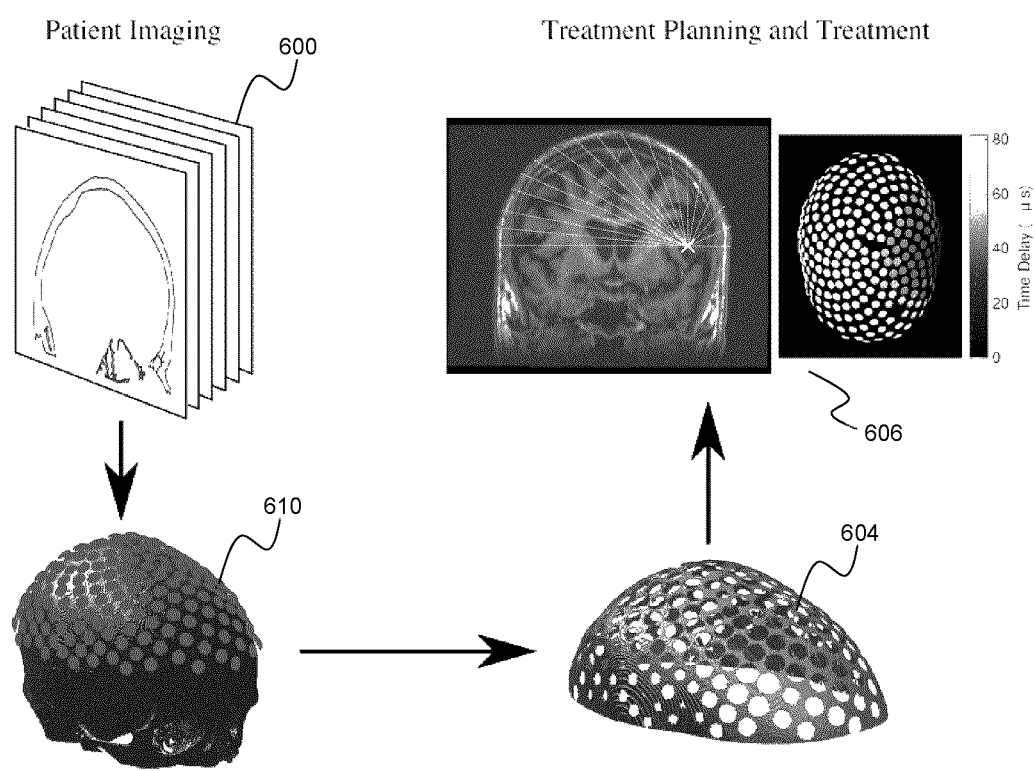
FIG. 4A illustrates an example process of design and construction a patient-specific array for transcranial focused ultrasound therapy.

FIG. 4A schematically illustrates the process of generating a patient-specific support (scaffold) for supporting the transcranial ultrasound transducer array elements, and optionally for the generation of a treatment plan for performing a transcranial focused ultrasound procedure.

As shown at 600, volumetric imaging of the patient is initially employed to determine the patient-specific skull profile. This patient-specific skull profile is then employed to determine the placement of the transcranial ultrasound transducer array elements around the head, as shown at 610. The calculated transcranial ultrasound transducer array element positions are then employed for placing the elements with the structure holding the elements or fabricate a patient-specific frame (an array support structure; scaffold) 610 that is configured to fit the patient's head. As described below, this patient-specific frame could be fabricated using rapid prototyping, and the support may include attachment interfaces for receiving and supporting the transcranial ultrasound transducer array elements. Finally, on the treatment day, the array would be fixed to the patient prior to the typical imaging sequence for target localization, followed by computer-assisted treatment planning and treatment.

The patient-specific frame 610 may include a plurality of attachment interfaces for receiving and supporting the transcranial ultrasound transducer array elements 500. For example, the attachment interfaces may be provided as apertures (recesses) into which the transcranial ultrasound transducer array elements 500 are placed. The transcranial ultrasound transducer array elements 500 may be affixed to the patient-specific frame 610 according to a wide variety of different means, such as with an attachment mechanism (e.g. via fasteners that extend into the patient-specific frame 610, optionally into pre-formed holes), or an adhesive such as a glue. The transcranial ultrasound transducer array elements may be remotely interfaced with electronics through wires or through a flexible printed circuit board. The transcranial ultrasound transducer array elements 500 may be removably attachable to the patient-specific frame 610.

The patient-specific headset may also include a coupling layer that is provided adjacent to an inner surface of the patient-specific frame. The outer surface of the coupling layer may contact distal surfaces of the transcranial ultrasound transducer array elements 500, and the inner surface of the coupling layer contacts the patient's head, thereby facilitating coupling of energy between the transducers in the patient-specific frame and the patient's head. The coupling layer may be an acoustic coupling layer that facilitates propagation of acoustic waves and reduces reflections at interfaces. In one example implementation, the coupling layer includes an elastic membrane that retains a liquid layer between the transducer surfaces and the elastic membrane, such that coupling to the skin is achieved.

The transcranial ultrasound transducer array elements, and their respective attachment interfaces, may have unique shapes (i.e. they may be respectively keyed), such that a given transcranial ultrasound transducer array element (e.g. its respective housing) fits uniquely with its respective attachment interface.

Figure 4B:
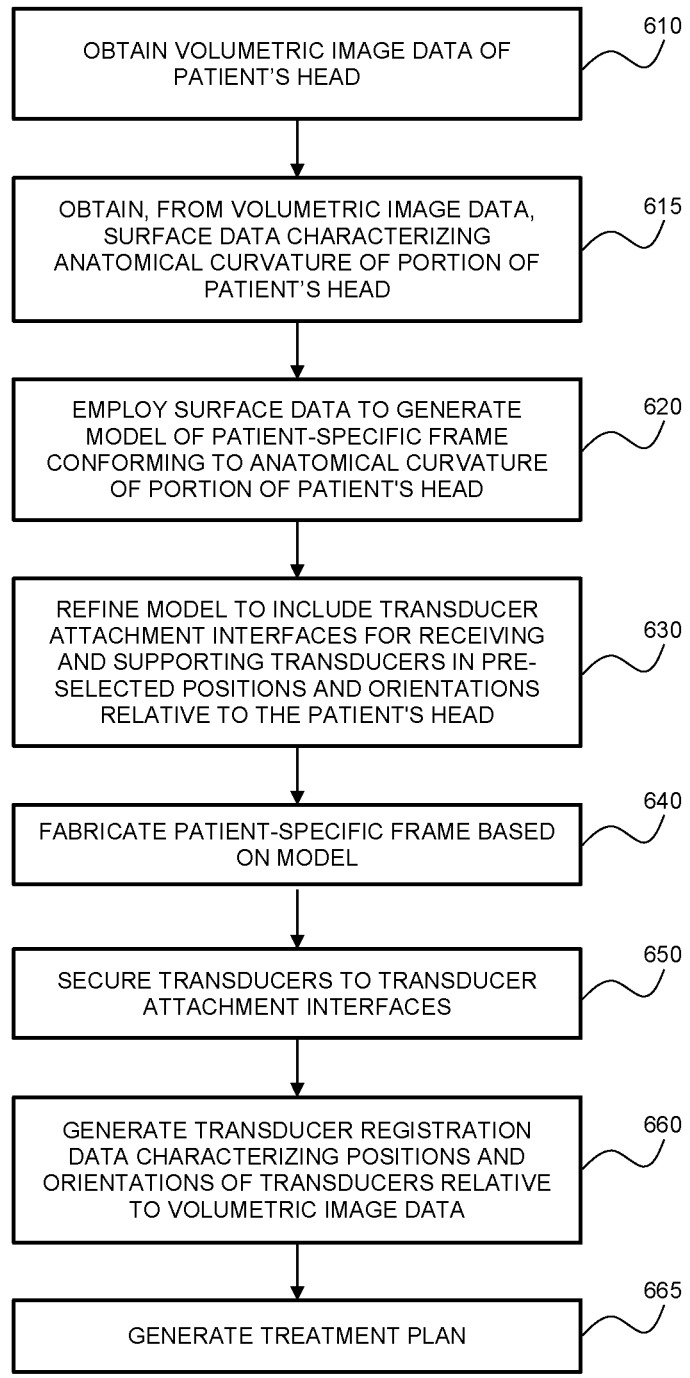
FIG. 4B is a flow chart illustrating an example method of fabricating a patient-specific headset.

As noted above, the patient-specific frame conforms to the anatomical contour of at least a portion of the patient's head. Such a conformal frame may be fabricated based on volumetric image data of the patient's head. FIG. 4B illustrates an example method for fabricating a patient-specific frame based on volumetric image data associated with the patient. In steps 610 and 615, volumetric image data of a patient's head is obtained and processed to provide surface data characterizing an anatomical curvature (e.g. skin or bone surface) of a portion of the patient's head. The volumetric data may be obtained, for example, by performing imaging using an imaging modality such as, but not limited to, magnetic resonance (MR) imaging and computed tomography (CT) imaging. The volumetric image data may be obtained based on a previously performed imaging procedure.

The volumetric image data may be processed and segmented to obtain surface data characterizing the surface of a portion of the patient's skull. Such surface segmentation may be performed, for example, using imaging processing software such as the Mimics™ software platform (Materialise, Belgium). Such software enables the creation of a 3D model (the surface data) of the surface of a portion of the patient's head. The model may be created using known techniques, such as using the steps of thresholding, region growing and manual editing. Automatic thresholding may be performed to achieve a first approximation of the skin surfaces of the skull, followed by manual editing to obtain a refined model. Haptic modeling, for example using a modeling software platform such as the PHANTOM™ Desktop Haptic Device, may be used to further refine the model. Additional example methods of image processing and segmentation of volumetric image data are disclosed in U.S. Pat. No. 8,086,336.

Subsequently, as shown in step 620, the surface data is used to produce a digital model to determine the placement of the transducer elements around the head of the patient. For example, a suitable software platform (such as the software package Surfacer™) may be employed to generate a model based on a point cloud of surface data points. This information can then be used to place the transducers, for example, when they are located in a holder that allows them to be moved in the desired locations. As shown at step 630, the model is then modified or refined (e.g. updated) to include a plurality of transducer attachment interfaces for receiving and supporting a plurality of transcranial ultrasound transducer array elements in pre-selected positions and orientations relative to the patient's head, and for supporting the transducers such that energy is coupled transcranially.

The positions and orientations of the transducer attachment interfaces may be determined as follows. Computer simulations can be used to calculate the wave propagation and select the positions from where the far-field of the transducers can reach the target location.

The digital model may be further refined to include one or more additional features, such as, but not limited to, an attachment interface for the attachment of one or more fiducial markers, an aperture to permit surgical access to a selected region of the patient's head when the patient-specific frame is worn (or otherwise placed on or around the head of the patient), markers for identifying reference directions, and one or more positioning features such as external handles.

The digital model, updated to include the transducer attachment interfaces, is then employed to fabricate the patient-specific frame, as shown at step 640. For example, the patient-specific frame may be fabricated from the model using 3D printing. In another example, the model may be employed to produce a mold suitable for forming the patient-specific frame, and the mold may be subsequently employed to fabricate the patient-specific frame.

After having fabricated the patient-specific frame, the transcranial ultrasound transducer array elements (or transducer array element assemblies or modules) are secured (attached, adhered, etc.) to the respective transducer attachment interfaces of the patient-specific frame, as shown at step 650.

In order to employ the patient-specific headset for performing diagnostic or therapeutic procedures based on pre-operative volumetric image data, a relationship may be established between the positions and orientations of the transcranial ultrasound transducer array elements and the volumetric image data (i.e. so that both can be represented within a common reference frame). Accordingly, in step 660, the known positions and orientations of the transcranial ultrasound transducer array elements (as prescribed in the digital model) are spatially registered relative to the volumetric image data, thereby generating transducer registration data characterizing the positions and orientations of the transducers relative to the volumetric image data. For example, such transducer registration data may include the spatial coordinates of the transcranial ultrasound transducer array elements, and vectors identifying their respective orientations, in the reference frame of the volumetric data. In another example implementation, the transducer registration data may include a coordinate transformation for transforming the positions and orientations of the transcranial ultrasound transducer array elements from a first reference frame to the reference frame of the volumetric image data. The transducer registration data enables the determination of the positions and orientations of the transcranial ultrasound transducer array elements relative to the volumetric image data, enabling, for example, the determination of suitable time and/or phase delays of transcranial ultrasound transducer array elements to focus, in the overlapping far field region, an energy beam at a specific location or region within the patient's head. The registration data, volumetric image data and the known positions and orientations of the transcranial ultrasound transducer array elements may then be employed to generate a treatment plan, as shown at 665.

In another embodiment, the registration between the frame and the head and brain can be achieved by performing imaging (for example MRI, CT, thomosynthesis, or x-ray) with the frame placed around the subject's head, allowing the transducer locations to be determined by imaging visible fiducial markers in the frame.

Although the preceding example embodiment involves the fabrication and use of a patient-specific frame that conforms to the anatomical curvature of the patient's head, it will be understood that this embodiment is included to provide one illustrative example of how the transcranial ultrasound transducer array elements may be supported.

According to another example implementation, the transcranial ultrasound transducer array elements may be supported by a support frame that does not have a patient specific shape, but is configured to support the plurality of transcranial ultrasound transducer array elements such that the transcranial ultrasound transducer array elements are adjustable. For example, the transcranial ultrasound transducer array elements may be manually or automatically adjustable relative to the support frame, in order to adjust the positions and orientations to match or approximate the positions and orientations calculated based on the volumetric image data associated with the patient. For example, the support frame may include one or more motors for varying the positions and/or orientations of the transcranial ultrasound transducer array elements. In some example implementations, the transducer may be held in place with rigid or flexible arms, holders, bands, or other suitable securing mechanisms.

While the example embodiments described above and in the following examples illustrate transcranial ultrasound transducer array configurations in which the transcranial ultrasound transducer array elements are focused within the skull, it will be understood that while intra-skull focusing may be beneficial in some implementations, other implementations may employ focusing configurations in which one or more of the transcranial ultrasound transducer array elements have a respective focal point that lies outside of, and adjacent to, the skull (e.g. adjacent to the inner or outer skull surfaces), such that the ultrasound beams that extends within the brain overlap in the far-field region.

Although some of the example embodiments described herein illustrate transcranial ultrasound transducer arrays having array elements with equal focal lengths, it will be understood that the focal lengths may differ among transcranial ultrasound transducer array elements, for example, in order to account for local variations in the skull thickness and/or shape. Furthermore, the sizes, spatial offsets relative to the skull, and/or F number of the transcranial ultrasound transducer array elements may vary among elements.

In some example embodiments, the transcranial ultrasound transducer array elements are configured and spatially arranged such that the far fields of each of the ultrasound beams overlap within a spatial region within the brain that permits the selection of a focusing target within an extended focusing region, such as the extended region shown in FIG. 3C. In other example embodiments, the transcranial ultrasound transducer array elements are configured and spatially arranged such that spatial overlap of the far field regions of the ultrasound beams occurs within a spatial region that includes a pre-selected target. In other words, the spatial configuration of the transcranial ultrasound transducer array elements may be selected based on a known target location within the brain.

Many of the example embodiments of the present disclosure pertain to the use of pulsed excitation and the control of the time delay (or phase) of the pulses from the transcranial ultrasound transducer array elements. However, although pulsed excitation may be beneficial in achieving a sharp focus, particularly for focal regions away from the natural focus of the transcranial ultrasound transducer array, continuous wave excitation of the transcranial ultrasound transducer array elements during delivery of focused ultrasound therapy, with appropriate phase control, may also be achieved in order to produce a focal region in the far field.

In some example embodiments, the transcranial ultrasound transducer array may be operated at two or more frequencies, such that different subsets of the transcranial ultrasound transducer array elements operate at different frequencies. For example, dual frequency excitation has shown promise in preclinical work to date in enhancing acoustic cavitation. As demonstrated in the examples provided below, tight focusing and dual-frequency excitation are also achievable according the present embodiments that employ far field focusing.

It will be understood that although the present disclosure includes many example embodiments pertaining to a transcranial ultrasound transducer array that is to be placed around the patient's head, the systems, devices and method disclosed herein may be adapted to provide a transcranial apparatus for performing diagnostic or therapeutic procedures on other parts or portions of the body. The support frame to support transducers for the far field focusing may be fabricated according to volumetric image data of other body regions or body portions. For example, a support frame may be fabricated, based on volumetric image data of a patient's knee, such that the support frame conforms to the contour of the patient's knee, for performing a diagnostic or therapeutic procedure on the knee using the transducer supported by the support frame. Similarly, a support frame may be fabricated, based on volumetric image data of a patient's spine, such that the support frame conforms to the contour of the patient's spine, for performing a diagnostic or therapeutic procedure on the spine using the transducer supported by the support frame. Furthermore, while many of the preceding examples embodiments pertain to the correction of skull-induced aberrations, the example embodiments described herein may be adapted to correct for aberrations produced in other bony anatomical regions of the body, such as, but not limited to, a kneecap or pelvic bone.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Materials and Methods

Skull Specimens:

Four human ex vivo skull caps fixed in 10% buffered formalin were used in the present example. Each skull was mounted in a polycarbonate frame and was rinsed with deionized water then degassed in degassed/deionized water under vacuum for at least two hours before the experiments. The four skull specimens had been imaged with a CT scanner previously as described in (Pichardo, Sin and Hynynen 2011) in order to have the skull thickness information for the resonance method and the density information for the CT-based aberration correction. The voxel dimensions were $0.625 \times 0.625 \times 0.625$ mm$^3$, and the image matrix was 512×512, with a total of 287-307 slices covering the skull cap.

Figure 5:
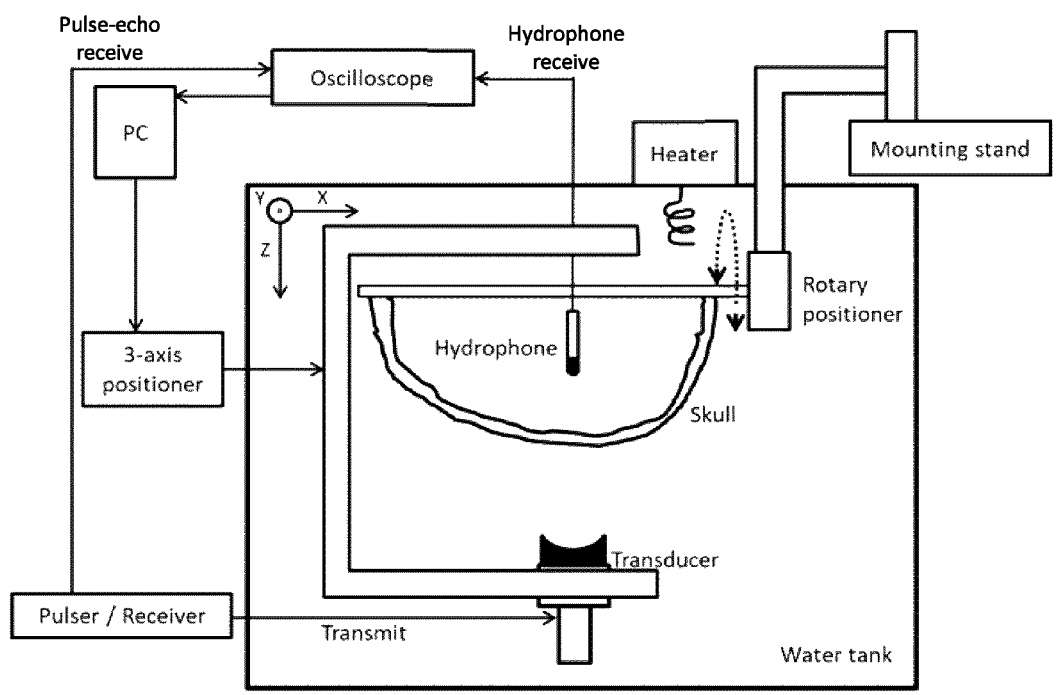
FIG. 5 is a schematic of an experimental setup for pulse-echo measurements based on the resonance method and hydrophone measurements.

Benchtop Experiments with Single Transducer:

A schematic of the experimental setup that was employed in the present example is shown in FIG. 5. A focused transducer (V389, Olympus, Center Valley, Pa., USA) was used in this study, with a fundamental frequency at 0.5 MHz, aperture of 38.1 mm, axial focal length of 55 mm, and lateral full-width-at-half-maximum of 6.8±0.3 mm. A hydrophone was fabricated in-house with a lead zirconate titanate (PZT) tube in a diameter of 1 mm and a height of 5 mm. The hydrophone and transducer were 65 mm apart, mounted and co-registered by an in-house-fabricated C-shaped holder, whose movement was controlled by a 3-axis positioning system with 2-phase stepping motors (PK266-03B-P2, VEXTA®, Oriental Motor Co., Ltd., Taito-Ku, Tokyo, Japan), stepping motor controllers (Velmex Inc., East Bloomfield, NY, USA) and an encoder (Quadra-Chek 100, Heidenhain, Schaumburg, IL, USA). Since normal incident angle of the ultrasound propagation is crucial to the measurement accuracy (Aarnio et al. 2004, White, Clement and Hynynen 2006), each skull specimen was positioned by a manual rotary positioner (Series 481-A, Newport, Irving, CA, USA) and a three-directional Cartesian positioning system (UniSlide® Assemblis Series A4000, Velmex Inc., East Bloomfield, NY, USA) until two separated peaks from the echoed signals could be seen on the oscilloscope (TDS 3012, Tektronix, Beaverton, OR, USA). The middle point between the outer and inner surfaces was placed at the focus of the transducer. The hydrophone was moved to at least four landmarks on the skull, which could be observed on the CT images. The corresponding coordinates were recorded using the 3-axis positioner, under the assumption that the coordinate of focus is (0, 0, 10). Two types of measurements were then performed.

Firstly, the resonance method was employed by emitting the transducer with a sharp delta-function pulse and receiving the pulse-echo signals reflected back from the targets with a Pulser/Receiver (DPR300, JSR Ultrasonics, Pittsford, NY, USA). The impulse response of the transducers was characterized by recording the pulse-echo signals from a water-air interface.

Secondly, the hydrophone method was applied by cross-correlating the time of flight of the pulsed signal received by the hydrophone with and without the presence of the skull.

This technique has served as the gold-standard method to determine the skull phase aberration corrections in several studies (Hynynen and Sun 1999, Clement and Hynynen 2002c, Gateau et al. 2010, Hertzberg et al. 2010, Jones et al. 2015). All the waveforms were captured by the oscilloscope (sample size: $10^4$, sampling frequency: 50 MHz) and transferred to the computer for further analysis with MATLAB™ (R2016b, Mathworks, Natick, MA, USA). All measurements were conducted in a tank with rubber-lined walls filled with degassed and deionized water.

Temperature Dependence of Skull Resonance Frequency:

The temperature of the water was heated and controlled by a heater (Thermomix® B, B. Braun Melsungen AG, Melsungen, Germany) from 25° C. to 42° C. with an increment of 3° C. Each skull sample was submerged in the water at the targeted temperature until steady state temperature was reached at each temperature. Both the resonance and hydrophone methods were employed to measure the phase shift of the ultrasonic wave induced by the skull at the selected skull locations.

Example 2: Data Analysis

Incident Angle Calculation and Skull Thickness Measurement from CT Data:

To register the skull CT with the experimental space, a transformation matrix, solved with the method described by Horn (Horn 1987), was applied to the CT data calculated from the positions of the landmarks in both of the CT and experimental coordinate systems. Registration accuracy was also tested by calculating the averaged distance between the experimental positions of the landmarks and the new positions transformed from CT data. In the present example measurement, this registration error is 0.6±0.4 mm across all four skulls.

CT image intensity in Hounsfield units was converted to a density map following a linear relationship illustrated in Connor et al. (Connor, Clement and Hynynen 2002). Skull segmentation was performed in MATLAB™ by thresholding the density and thus only the voxels related to skull bones were shown. The incident angles of the ultrasonic impulse at the outer and inner surfaces of the skulls were calculated by using the triangular-meshed skull surface data which were generated from CT segmentation following the procedure outlined in Jones et al. (Jones, O'Reilly and Hynynen 2013). The incident ray represented by a vector from the center of the transducer to the target was defined and discretized with a step size a quarter of the CT voxel resolution 0.625 mm. The distance from every point along this ray to the centroid of every triangle on the meshed skull surfaces was calculated and the triangles with shortest distance were found. The incident angle to the skull surface at the closest triangle to the transducer center was determined.

The thickness of the skull was calculated from the CT data based on the "new fixed" method introduced in Treece's study (Treece et al. 2010). In brief, the density along the incident ray through the skull can be modeled as a convolution of the density with an in-plane and out-of-plane point spread function (PSF). The density y over distance x can be expressed as follows (Treece et al. 2010):

$$y(x)=y_0+(y_1-y_0)H(x-x_0)+(y_2-y_1)H(x-x_1) \quad (6)$$

where $y_0$, $y_1$, $y_2$ are the density of water, cortical and trabecular bone, respectively, $x_0$ and $x_1$ are the locations of outer and inner skull surfaces, and H(x) is a step function. The in-plane PSF $g_i$ can be modeled as the follows:

$$g_i(x) = \frac{e^{\frac{x^2}{\sigma^2}}}{\sigma\sqrt{\pi}}, \quad (7)$$

where σ is the blur extension. The out-of-plane PSF can be expressed as a rectangular function:

$$g_0(x) = \frac{1}{2r}[H(x+r) - H(x-r)], \quad (8)$$

where 2r represents the extent of uncertainty, calculated from the CT slice thickness s and the angle a between the cortical surface normal and the imaging plane, given by the following equation:

$$r = \frac{s}{2}\tan a. \quad (9)$$

Convoluting Eqn. (6) with (7) and (8), the blurred CT values $y_{blur}$ are denoted by:

$$y_{blur}(x) = y_0 + \int\int \frac{y_1 - y_0}{2r\sigma\sqrt{\pi}}\left[e^{-\frac{(x+r-x_0)^2}{\sigma^2}} - e^{-\frac{(x-r-x_0)^2}{\sigma^2}}\right] + \frac{y_2 - y_1}{2r\sigma\sqrt{\pi}}\left[e^{-\frac{(x+r-x_1)^2}{\sigma^2}} - e^{-\frac{(x-r-x_1)^2}{\sigma^2}}\right]dxdx. \quad (10)$$

When r=0, Eqn. (10) will be modified to:

$$y_{blur,r=0}(x) = y_0 + \int \frac{y_1 - y_0}{\sigma\sqrt{\pi}}e^{-\frac{(x-x_0)^2}{\sigma^2}} + \frac{y_2 - y_1}{\sigma\sqrt{\pi}}e^{-\frac{(x-x_1)^2}{\sigma^2}}. \quad (11)$$

The skull thickness d is then:

$$d=(x_1-x_0)\cos a. \quad (12)$$

CT data was transformed from the CT coordinates system to the experimental coordinates system by applying the transformation matrix from skull registration. The lines passing through the skull bones from the center of the transducer to the targets were spline-interpolated 100 times, which was later fitted with the model of Eqn. (11) in order to estimate the edges of the cortical layer ($x_0$, $x_1$), assuming r=0 (i.e., the cortical layer lie orthogonal to the CT imaging plane). In the process of optimization, the density of water $y_0$ was determined from the histogram of the CT images. $y_2$ (the density of the trabecular bone) was left free for the model to discover due to the fact that its density varies at different locations. The in-plane extent of uncertainty σ was unconstrained and the cortical density $y_1$ was set within the range of [2000, 3000].

CT-Based Phase Correction:

An analytical method based on Clement's study (Clement and Hynynen 2002a) was used to simulate the phase shifted induced by skull based on the CT-derived skull density, thickness and the orientation with respect to the transducer in the experimental setup, similar to the technique employed in Jones & Hynynen (Jones and Hynynen 2016) for transcranial passive acoustic imaging. The longitudinal speed of sound in skull is density dependent based on the empirical relation in previous study (Pichardo et al. 2011). The time of flight in skull bone was determined by calculating longitudinal sound speed profile within the skull along the incident ray between the center of the transducer and the target, neglecting both reflection and refraction effects. As a result, the time delay caused by the presence of skull can be represented as the time-of-flight difference between the trans-skull and water-path cases:

$$t = \int_0^{D_n} \frac{dr}{c_b(\rho(r))} - \frac{D_n}{c_w}, \quad (13)$$

where $D_n$ is the length of the ray within the skull. The phase shift can then be calculated with Eqn. (4).

Example 3: Results 784 target spots were measured on four ex vivo human skulls caps ($n_{sk1}$=276, $n_{sk2}$=151, $n_{sk3}$=148, $n_{sk4}$=209). An example of the radiofrequency signal reflected back from one target spot on Sk2 is shown in FIG. 6A, and the corresponding normalized frequency spectrum before and after deconvolution are displayed in FIGS. 6B and 6C. The speed of sound in skull bone can be calculated by measuring the locations of the minima and applying the frequency difference of the adjacent minima to Eqn. (5).

The reflected-calculated phase shifts based on the resonance method were compared to the hydrophone method in FIG. 7A. The mean difference between the two modalities is 33°±26°. A histogram of the phase shift difference is shown in FIG. 7B. In 72.9% of the 784 measurements the two modalities differed by less than 45°, and in 37.1% by less than 20°. By excluding the spots with incident angles on the outer surface larger than 5°, 80.4% of the 403 measured spots had the phase shift difference less than 45°, and 42.9% by less than 20°, as shown in FIGS. 7C and 7D.

Figure 8A:
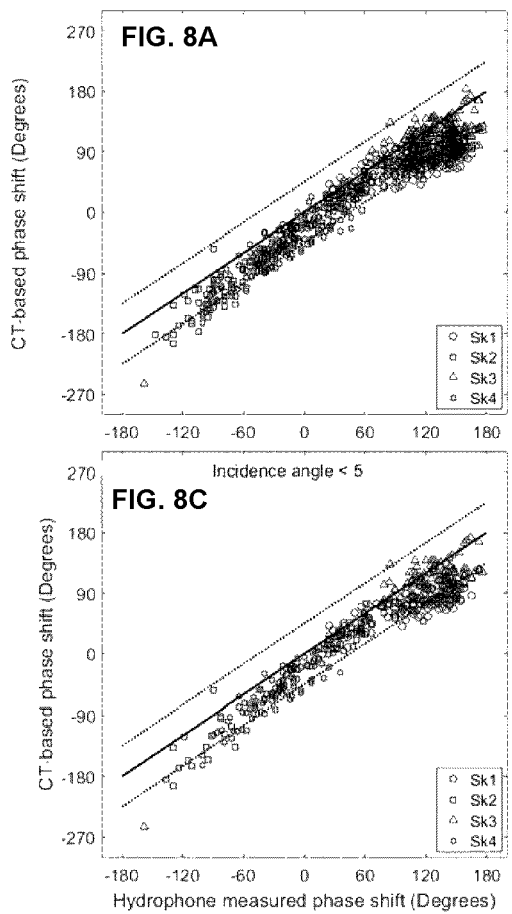
FIG. 8A-8D plot (FIG. 8A) CT-based phase shifts as a function of hydrophone-measured phase shifts.
Figure 8B:
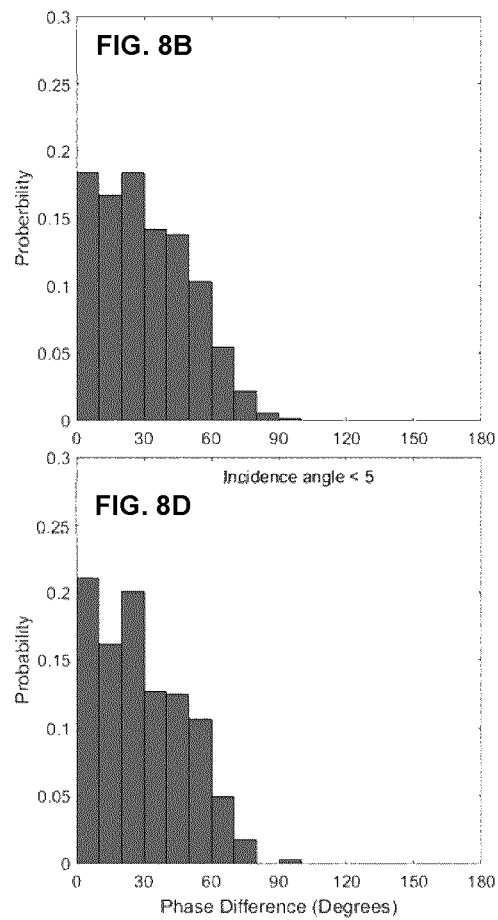
Figure 8C:
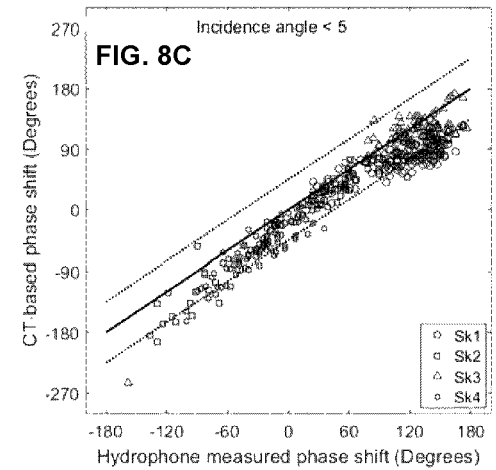
Figure 8D:
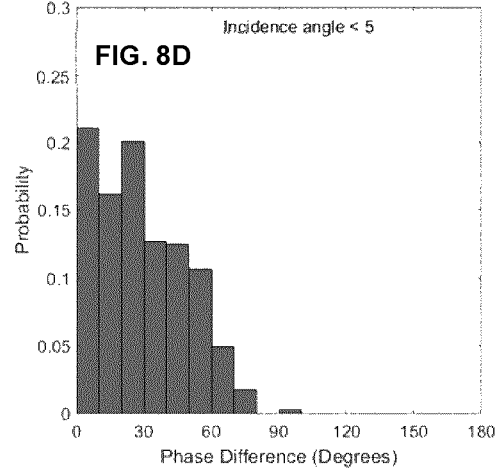
Figure 12:
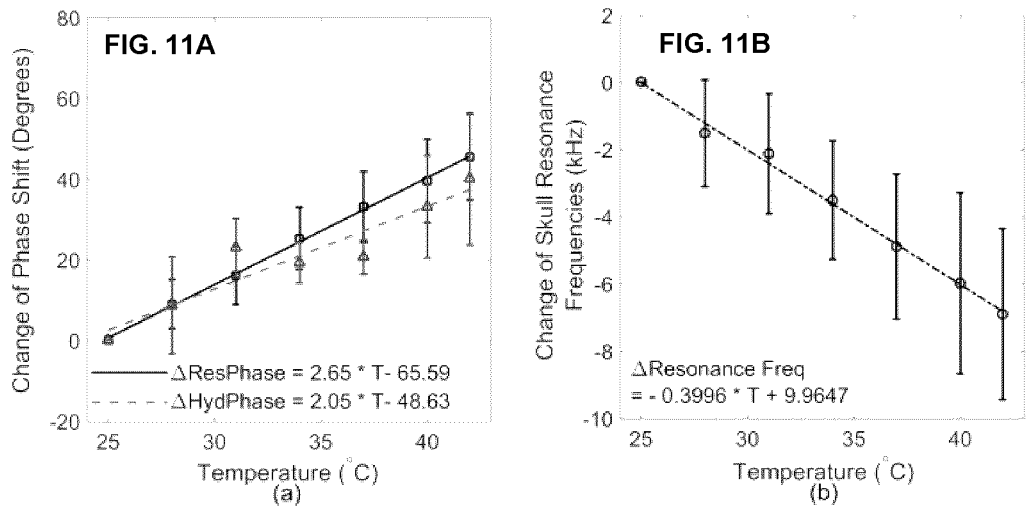
FIG. 12 is a table providing values for the mean thickness, incident angles and the percentage of phase difference less than 45° and 20° of all the measured spots on skulls 1-4 ($n_{total}$=784).

The phase shifts calculated from CT-based method with analytical model as a function of the hydrophone-measured phase shift are presented in FIGS. 8A and 8C. There is a systematic shift for the CT-based analytical method as it can be seen that most of the markers are within the region between 0 and −45°. The mean difference between the two modalities is 31°±20°, which slightly drops to 29°±19° when the spots with incident angles larger than 5° have been excluded. 74.5% of the measurements have the phase shift difference between the two methods less than 45°, and 35.1% by less than 20° FIGS. 8B and 8D. Skull thickness, incident angles and the percentage of phase shift difference have been summarized in FIG. 12. Resonance method provides similar results as the CT-based analytical method in general, although the accuracy varies from skull to skull.

Figures 9A, 9B:
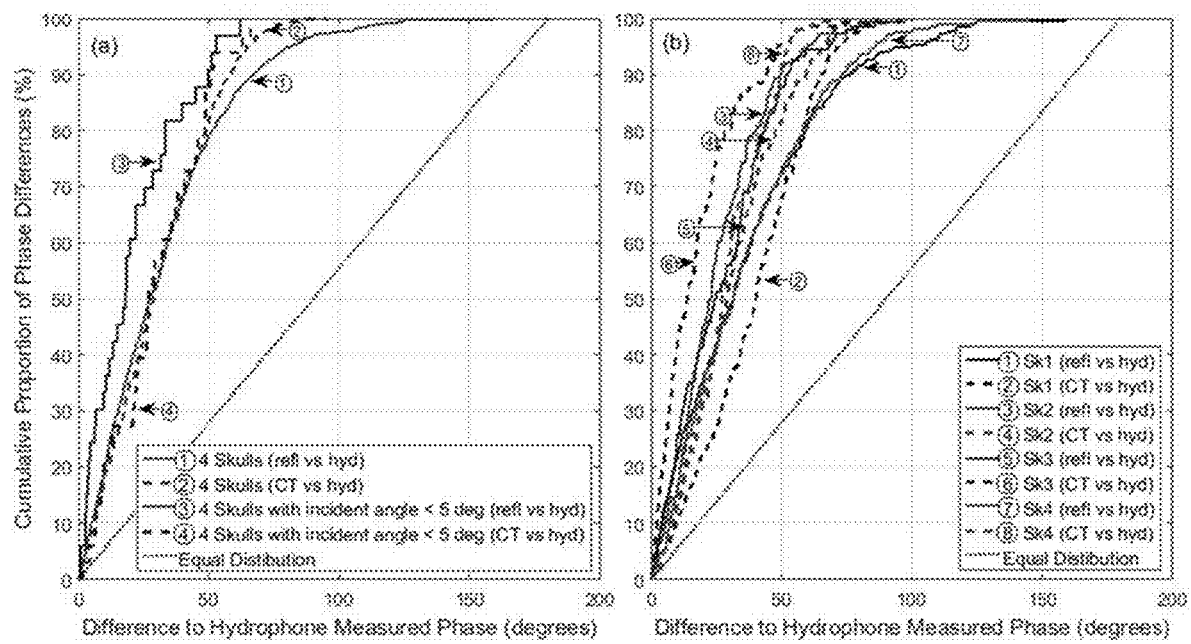
FIGS. 9A-9B plot cumulative proportion of the phase differences of the three modalities (solid line: resonance vs. hydrophone method; dashed line: CT-based correction vs. hydrophone method) for all the spots measured, showing (FIG. 9A) all 4 skulls were represented with red line, the case with incident angle less than 5° with blue line, and (FIG. 9B) skull 1-4 with black, red, blue, and magenta lines, correspondingly. Equal distribution was marked with dotted line. Ideally the graph would be a step function.

Additional information is revealed in FIGS. 9A and 9B, which shows the percent of measured points with a deviation smaller than a given phase angle difference from the three modalities. A sharp rise indicates good correlation between the resonance method and the hydrophone method. FIG. 9A illustrates the overall comparison of resonance and CT-based methods relative to the hydrophone. Resonance method with incident angle less than ° has a slightly sharper rise than the CT-based one. Specific cases were displayed in FIG. 9B. The measurements on each skull plotted in terms of this deviation illustrate better correlation on Sk2 & Sk3, with 86.1% and 82.4% differing by less than 45°, respectively, and 45.0% and 42.0% less than 20°, respectively, as opposed to an around 67% of the spots with deviation less than 45° and approximately 35% less than 20° on Sk1 and Sk4.

Figure 10A:
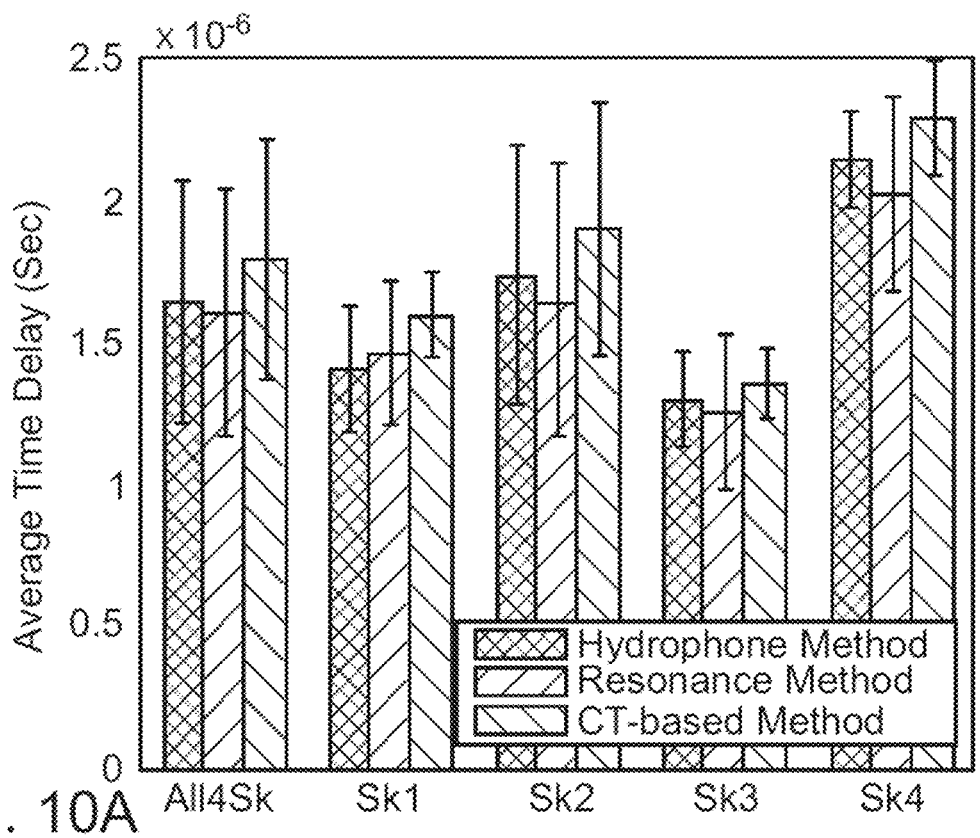
FIGS. 10A-10B plot a comparison of (FIG. 10A) the average time delay and (FIG. 10B) the speed of sound in skull bones calculated from hydrophone and resonance method (n=403). "AllSk" represents the average time delay and speed of sound for all 4 skulls.
Figure 10B:
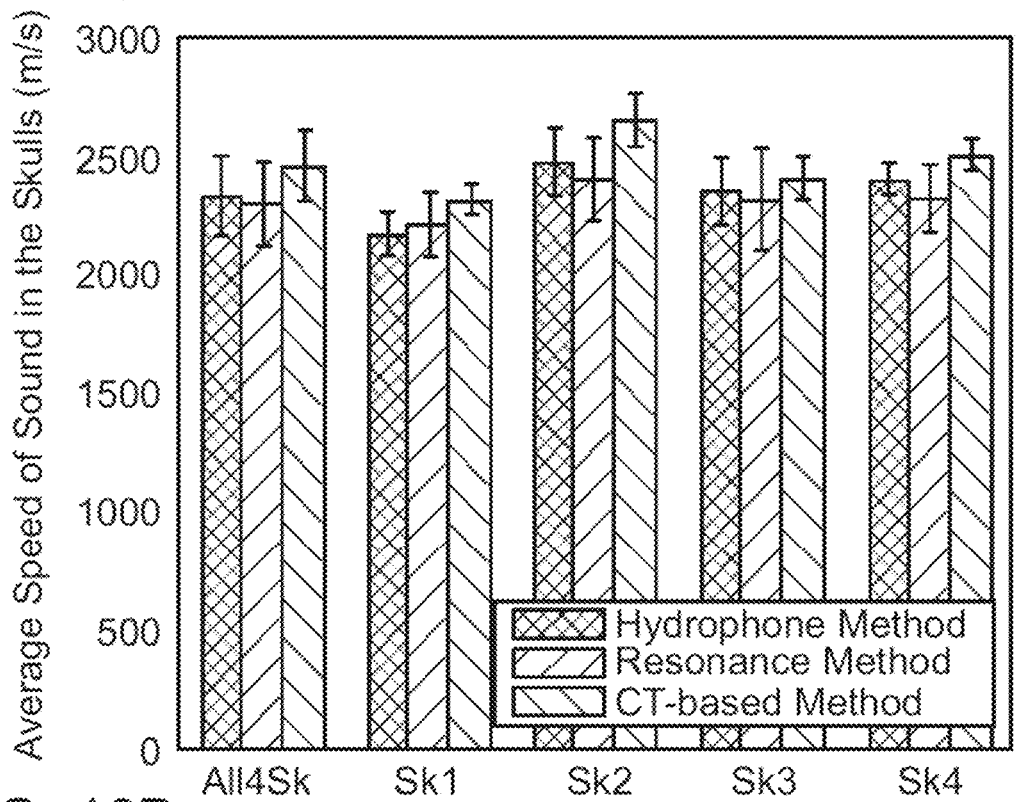

Comparison of the resonance/CT methods to the hydrophone method in terms of the calculated average time delays induced by the skull and SoS in skull bones are shown in FIGS. 10A and 10B. It is illustrated that the resonance method produces a closer time delay and speed of sound estimation than the CT-based method.

The information of the skull phase shift difference between the resonance/CT methods and the hydrophone method allows an estimation of the reduction of transcranial peak acoustic pressure. As to a phase array with N elements, assuming the peak amplitudes with the hydrophone phase correction through each element are the same and all normalized to 1, the peak pressure amplitude at the focus will be reduced by a percentage (Clement and Hynynen 2002a):

$$\frac{\Delta P}{P_0} = 1 - \frac{\left|\sum_{n=1}^{N} e^{i\varnothing n}\right|}{N},$$

(13) where $\Delta P$ is the pressure loss, $P_0$ is the peak pressure at the focus with hydrophone method, $\varnothing_n$ is the absolute value of the phase error induced by the inaccurate prediction of the skull phase shift from the resonance/CT-based analytical methods. With the resonance method, there is a 6.7%, 4.4%, 5.6%, and 10.8% of peak pressure reduction, as opposed to a smaller pressure loss of 2.4%, 5.5%, 4.9%, and 3.5% with the CT method on the skulls Sk1, Sk2, Sk3, and Sk4, correspondingly. Measurements of the skull phase shift with temperature elevated from 25° C. to 42° C. were performed with both resonance and hydrophone methods. The mean change in phase from all 4 skull samples between room temperature and 42° C. as a function of temperature at 0.5 MHz has been shown in FIG. 11A. The resonance method produced 2.65° of phase change per° C., slightly higher than 2.05° as given by the hydrophone method. The change of mean resonant frequencies of skulls is proportional to the variation of temperature with a negative coefficient, as illustrated in FIG. 11B.

The phase shift was measured at each spot with elevated temperature using both the resonance and hydrophone methods. No sharp decrease in the accuracy was observed during the temperature elevation. The accuracy obtained under each temperature from each skull and all 4 skulls was averaged. The mean accuracy across the 17° C. temperature difference is 78%±9% for all the measured points.

Example 4: Analysis

This study explored the factors that may improve the accuracy of resonance method in determining the ultrasound phase shift induced by the skull bone. The results show that approximately 73% and 37% of all measured points ($n_{total}$=784) deviate by less than 45° and 20°, respectively, when comparing the resonance method to the hydrophone method, which were increased from nearly 65% and 30% in the previous study (Aarnio et al. 2005). The mean difference of the phase shifts between the two modalities is 30.5°, approximately 15° less than the Aarnio's study (Aarnio et al.

2005). This decreased difference demonstrates a higher accuracy in phase aberration correction with the modified resonance method.

The improvement of accuracy may first of all come from the experimental configuration that the focus of the transducer was centered within the skull. It benefits from both a small field size and large aperture resulting in smaller measurement discrepancy in geometry interfering with skull and a higher signal-to-noise ratio (SNR), than the earlier study (Aarnio et al. 2004). Secondly, the incident angle of the ultrasound burst plays an important role in the measurement accuracy. It has been shown that the frequency spectra deteriorated rapidly with an increasing incident angle (Aarnio et al. 2004, White et al. 2006), which induced extra difficulties to detect the resonant frequencies. By excluding the measured spots with incident angle 5° (n=403), about 80% of the measurements had a deviation of 45° or less. Comparing the SoS in skull predicted by the two modalities, the resonance method offered 2310±180 m/s, approximately 1.3% lower than the mean sound speed 2340±170 m/s given by the hydrophone method, as opposed to 5.8% higher in the previous study (Aarnio et al. 2005).

The skull thickness calculated from the CT data also has an impact on the accuracy and practicality of the method. In the present study, the resolution of the CT image (0.625 mm) is close to a quarter of the wavelength of the transducer center frequency (0.75 mm), which means that one voxel difference may lead to an almost 45° phase changing. With the given resolution, it is necessary to interpolate the CT data and fit it with an optimized model in order to provide accurate skull thickness estimation. Two algorithms "Half-Max" and "New Fixed" described in Treece's study (Treece et al. 2010) have been tested. "Half-Max" provided better thickness estimation on Sk2 and Sk4, but less accurate in predicting thin skulls Sk1 & Sk3 (skulls thickness summarized in FIG. 12). Yet, "New Fixed" was more accurate with thin skull cases. This result matched with the simulation in Treece's study, which displays that the "Half-Max" method tends to overestimate the thickness of the cortical bone thinner than 2.2 mm, especially under the circumstance that the CT resolution is low, resulting in a systematic shift in the resonance-method calculated phase shift. In the present study, the thickness of cortical bone on Sk1 & Sk3 is less than 2.2 mm, which explains why the "New Fixed" method provides better thickness estimation. Eventually, the "New fixed" technique has been employed in the present study.

The results of the present experiments have confirmed that using a lower frequency transducer helped improve the measurement accuracy from 65% (at 0.9 MHz) (Aarnio et al. 2005) to 73% (at 0.5 MHz), resulting from a lower attenuation rate at 0.5 MHz through skull (Sun and Hynynen 1998) and an increase SNR in the data. Furthermore, it is less impacted by the incident angle. However, there is a trade-off between the low center frequency and wide bandwidth. The narrow bandwidth brought in by the low frequency increases the difficulty to determine the resonance frequencies on thin skulls. The bandwidth of transducer in the present study is in the range of [0.3, 0.8] MHz, which is much narrower than the range [0.6, 1.74] MHz in the previous work (Aarnio et al. 2005), which made it difficult in measuring the resonant frequencies with Sk1 & Sk3.

Although it is demonstrated that the accuracy of the resonance method has been improved, there are still some outliers distributed out of the constructive interference region, even in the normal incidence cases, as shown on FIG. 7C. Several factors might cause the errors when using the resonance method. First, by comparing the "New Fixed" fitting in the skull thickness calculation to the CT density profiles along the ultrasound wave propagation paths at the locations with big errors, it was found that with the thick skulls the "New Fixed" method (Treece et al. 2010) sometimes failed to find the correct boundaries of the cortical bone, resulting in the inaccuracy of the calculated phase shift. This phenomenon matches with Treece's simulation that the "New Fixed" fitting tends to give a slightly bigger error compared to the true value when the cortical bone thickness is over 3.5 mm, but it is less sensitive to the cortical bone thickness overall compared to the other fitting methods. Additionally, the heterogeneity of the skull also introduced error into the calculation. By going through the CT slices adjacent to the outliers, it was found that at some locations the skull structure was not consistent within the focal region (FWHM: 6.8±0.3 mm), where a sharp drop of the trabecular bone density was shown. Since the phase shift information given by the resonance method was a combination of multiple reflection paths, the big change in bone density may cause a big error, while compared to the hydrophone and CT-based analytical methods that are based on single path transmission with simplified skull structure.

It was therefore determined that in order to further improve the accuracy of the resonance method, a transducer with a smaller focus may be employed, in order to avoid a large variance from skull structure and to keep the assumption of flat skull surface valid.

A direct comparison of the resonance method to the other non-invasive method such as CT-based analytical model has been presented. In general, the resonance method offers a slightly better prediction of the skull phase shift as the CT-based analytical model in terms of the distribution of phase discrepancy compared to the gold-standard method, as demonstrated in FIG. 9A. The resonance-calculated phase shifts seem to be unbiasedly distributed along the main diagonal as presented in FIGS. 7A and 7C, offering a better accuracy than the CT-based analytical method, in which a systematic shift can be seen in the phase lag as displayed in FIGS. 8A and 8C. In the CT-based analytical model, although spline-interpolation has been performed along the incident ray through skull and the SoS is density dependent based on the density profile given by the fitting (Pichardo et al. 2011), it might be still ambiguous to define the boundaries of the cortical bones limited by the low CT imaging resolution and thus the thickness is over estimated especially when the thickness is small, similar to the results given by the 'Half-Max' method (Treece et al. 2010). Besides, the parameter such as longitudinal SoS in bone used in the analytical model was empirical, and the skull has been simplified to a multi-layer model, resulting in similar predictions of skull phase shift to the resonance method.

As noted above, previous work has shown that the change of skull phase shift measured with hydrophone as a function of temperature follows a linear fit with a slowly increasing rate of 0.29° of phase per ° C., leading to a total phase shift change less than 14° when the temperature was elevated from 22° C. to 50° C. (Clement and Hynynen 2002a). As a result, conclusions have been drawn that the increased temperature would not significantly affect the phase shift change and thus the phase shift measured at room temperature can be applied to the skull phase correction at body temperature. However, the temperature control was not performed in that study. Skull samples were heated in a separated water tank and were transferred into the experimental setup when temperature reached the set value. Heat diffusion would occur once skulls were placed in the water at room temperature thus decreasing the actual skull temperature in the measurement. In our study, modification has been made so that temperature control and skull phase shift measurements were performed in the same experimental setup. Both resonance (2.65°/° C.) and hydrophone methods (2.05°/° C.) were found to produce higher slopes than the previous study (see FIG. 11A). It follows that it may be beneficial to compensate the change of phase shift due to thermal deposition, since a 10° C. increase in high intensity ultrasound sonications leads to approximately 20° C. variation in phase and about 39% of the phase correction shifted out of the constructive interference region.

Secondly, the present results (FIG. 11A) shows that, in general, the resonance method provides a higher slope than the hydrophone method. The resonance method relies on the impulse-echoed signals from multiple paths, and thus more variation in term of skull density and incident angles during the temperature elevation process was expected, as opposed to the hydrophone measurement based on single path transmission.

Thirdly, it has been found that the resonance method provides a better linear fit to the phase shift dependency of temperature change in all of the skulls tested than the hydrophone method. Last but not least, the accuracy of the resonance method in determining the skull phase shift during temperature elevation has been summarized as compared to the standard hydrophone method. No obvious trend of accuracy decreasing with an increase of temperature has been observed on the skull, and the averaged accuracy was able to be maintained at 78%±9% (n=110).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

Aarnio, J., G. T. Clement & K. Hynynen (2004) Accuracy of the resonance ultrasound method in determination of the acoustic phase shifts in plastic and bone. *IEEE 2004 Ultrason. Symp.,* 3, 1800-1803.
  (2005) A new ultrasound method for determining the acoustic phase shifts caused by the skull bone. *Ultrasound Med. Biol.,* 31, 771-80.
Aubry, J. F., M. Tanter, J. Gerber, J. L. Thomas & M. Fink (2001) Optimal focusing by spatio-temporal inverse filter. II. Experiments. Application to focusing through absorbing and reverberating media. *J. Acous.t Soc. Am.,* 110, 48-58.
Aubry, J. F., M. Tanter, M. Pernot, J. L. Thomas & M. Fink (2003) Experimental demonstration of noninvasive transskull adaptive focusing based on prior computed tomography scans. *J. Acoust. Soc. Am.,* 113, 84-93.
Besl, P. J., & McKay, N. D. (1992) A method for registration of 3-D shapes. *IEEE Trans. Pattern. Anal. Mach. Intel.l,* 14(2), 239-56.
Bonfield, W. & A. E. Tully (1982) Ultrasonic analysis of the Youngs modulus of cortical bone. *J. Biomed. Eng.,* 4, 23-7.
Clement, G. T. & K. Hynynen (2002a) Correlation of ultrasound phase with physical skull properties. *Ultrasound Med. Biol.,* 28, 617-624.
Clement, G. T. & K. Hynynen (2002b) Micro-receiver guided transcranial beam steering. *IEEE Trans. Ultrason. Ferroelectr. Freq. Control,* 49, 447-53.
  (2002c) A non-invasive method for focusing ultrasound through the human skull. *Phys. Med. Biol.,* 47, 1219-36.
Coluccia, D., J. Fandino, L. Schwyzer, R. O'Gorman, L. Remonda, J. Anon, E. Martin & B. Werner (2014) First noninvasive thermal ablation of a brain tumor with MR-guided focused ultrasound. *J. Ther. Ultrasound,* 2, 17.
Connor, C. W., G. T. Clement & K. Hynynen (2002) A unified model for the speed of sound in cranial bone based on genetic algorithm optimization. *Phys. Med. Biol.,* 47, 3925-44.
Connor, C. W. & K. Hynynen (2004) Patterns of thermal deposition in the skull during transcranial focused ultrasound surgery. *IEEE Trans. Biomed. Eng.,* 51, 1693-706.
Elias, W. J., D. Huss, T. Voss, J. Loomba, M. Khaled, E. Zadicario, R. C. Frysinger, S. A. Sperling, S. Wylie, S. J. Monteith, J. Druzgal, B. B. Shah, M. Harrison & M. Wintermark (2013) A pilot study of focused ultrasound thalamotomy for essential tremor. *N. Engl. J. Med.,* 369, 640-8.
Elias, W. J., N. Lipsman, W. G. Ondo, P. Ghanouni, Y. G. Kim, W. Lee, M. Schwartz, K. Hynynen, A. M. Lozano, B. B. Shah, D. Huss, R. F. Dallapiazza, R. Gwinn, J. Witt, S. Ro, H. M. Eisenberg, P. S. Fishman, D. Gandhi, C. H. Halpern, R. Chuang, K. Butts Pauly, T. S. Tierney, M. T. Hayes, G. R. Cosgrove, T. Yamaguchi, K. Abe, T. Taira & J. W. Chang (2016) A Randomized Trial of Focused Ultrasound Thalamotomy for Essential Tremor. *N. Engl. J. Med.,* 375, 730-9.
Flax, S. W. & M. O'Donnell (1988) Phase aberration correction using signals from point reflectors and diffuse scatterers: Basic principles. *IEEE Trans. Ultason. Ferroelec. Freq. Contr.,* 35, 758-767.
Fry, F. J. & J. E. Barger (1978) Acoustical properties of the human skull. *J. Acoust. Soc. Am.,* 63, 1576-1590.
Gateau, J., L. Marsac, M. Pernot, J. F. Aubry, M. Tanter & M. Fink (2010) Transcranial ultrasonic therapy based on time reversal of acoustically induced cavitation bubble signature. *IEEE Trans. Biomed. Eng.,* 57, 134-144.
Guyott, C. H. H. C., P. (1988) The measurement of through thickness plate vibration using a pulsed ultrasound transducer. *J. Acoust. Soc. Am.,* 83, 9.
Hertzberg, Y., A. Volovick, Y. Zur, Y. Medan, S. Vitek & G. Navon (2010) Ultrasound focusing using magnetic resonance acoustic radiation force imaging: application to ultrasound transcranial therapy. *Med. Phys.,* 37, 2934-42.
Horn, B. K. P. (1987) Closed-form solution of absolute orientation using unit quaternions. *J. Opt. Soc. Am.,* A4, 629-642, 14.
Hughes, A. & K. Hynynen (2017) Design of patient-specific focused ultrasound arrays for non-invasive brain therapy with increased trans-skull transmission and steering range. *Phys. Med. Biol.,* 62, L9-L19.
Hynynen, K., N. McDannold, G. Clement, F. A. Jolesz, E. Zadicario, R. Killiany, T. Moore & D. Rosen (2006) Pre-clinical testing of a phased array ultrasound system for MRI-guided noninvasive surgery of the brain—a primate study. *Eur. J. Radiol.,* 59, 149-56.
Hynynen, K. & J. Sun (1999) Trans-skull ultrasound therapy: the feasibility of using image-derived skull thickness information to correct the phase distortion. *IEEE Trans. Ultrason. Ferroelectr. Freq. Control.,* 46, 752-5.
Jeanmonod, D., B. Werner, A. Morel, L. Michels, E. Zadicario, G. Schiff & E. Martin (2012) Transcranial magnetic resonance imaging-guided focused ultrasound: noninvasive central lateral thalamotomy for chronic neuropathic pain. *Neurosurg Focus*, 32, E1.

Jones, R. M. & K. Hynynen (2016) Comparison of analytical and numerical approaches for CT-based aberration correction in transcranial passive acoustic imaging. *Phys. Med. Biol.*, 61, 23-36.

Jones, R. M., M. A. O'Reilly & K. Hynynen (2013) Transcranial passive acoustic mapping with hemispherical sparse arrays using CT-based skull-specific aberration corrections: a simulation study. *Phys. Med. Biol.*, 58, 4981-5005.

(2015) Experimental demonstration of passive acoustic imaging in the human skull cavity using CT-based aberration corrections. *Med. Phys.*, 42, 4385-400.

Jung, H. H., S. J. Kim, D. Roh, J. G. Chang, W. S. Chang, E. J. Kweon, C. H. Kim & J. W. Chang (2015) Bilateral thermal capsulotomy with MR-guided focused ultrasound for patients with treatment-refractory obsessive-compulsive disorder: a proof-of-concept study. *Mol. Psychiatry*, 20, 1205-11.

Kim, M., C. H. Kim, H. H. Jung, S. J. Kim & J. W. Chang (2018) Treatment of Major Depressive Disorder via Magnetic Resonance-Guided Focused Ultrasound Surgery. *Biol. Psychiatry*, 83, el 7-el 8.

Kinsler, L. E. & A. R. Frey. 1962. *Fundamentals of acoustics*. New York: Wiley.

Lipsman, N., M. L. Schwartz, Y. Huang, L. Lee, T. Sankar, M. Chapman, K. Hynynen & A. M. Lozano (2013) MR-guided focused ultrasound thalamotomy for essential tremor: a proof-of-concept study. *Lancet Neurol.*, 12, 462-8.

Martin, E., D. Jeanmonod, A. Morel, E. Zadicario & B. Werner (2009) High-intensity focused ultrasound for non-invasive functional neurosurgery. *Ann. Neurol.*, 66, 858-61.

McDannold, N., G. T. Clement, P. Black, F. Jolesz & K. Hynynen (2010) Transcranial magnetic resonance imaging-guided focused ultrasound surgery of brain tumors: initial findings in 3 patients. *Neurosurgery*, 66, 323-332.

Nocl, L., G. E. Trahey & S. W. Smith (1989) Phase aberration correction in medical ultrasound using speckle brightness as a quality factor. *J. Acoust. Soc. Amer.*, 85, 1819-1833.

O'Donnell, M. & S. W. Flax (1988) Phase aberration correction using signals from point reflectors and diffuse scatterers: Measurements. *IEEE Trans. Ultrason. Ferroelec. Freq. Contr.*, 35, 768-774.

Ohkawai, H. N., S.-I.; Tanaka, M.; Dunn, F. (1983) In vivo measurement of thickness or of speed of sound in biological tissue structures. *IEEE Trans. Sonics. Ultrason.*, SU-30, 7.

O'Reilly, M. A., Jones, R. M., Birman, G. & Hynynen, K. (2016) Registration of human skull computed tomography data to an ultrasound treatment space using a sparse high frequency ultrasound hemispherical array. *Med. Phys.*, 43, 5063-71

Pichardo, S., V. W. Sin & K. Hynynen (2011) Multi-frequency characterization of the speed of sound and attenuation coefficient for longitudinal transmission of freshly excised human skulls. *Phys. Med. Biol.*, 56, 219-50.

Seip, R., P. VanBaren & E. S. Ebbini (1994) Dynamic focusing in ultrasound hyperthermia treatments using implantable hydrophone arrays. *IEEE Trans. Ultrason. Ferroelec. Freq. Control*, 41, 706-713.

Sun, J. & K. Hynynen (1998) Focusing of therapeutic ultrasound through a human skull: a numerical study. *J. Acoust. Soc. Am.*, 104, 1705-15.

Tanter, M., J. L. Thomas & M. Fink (1998) Focusing and steering through absorbing and aberrating layers: application to ultrasonic propagation through the skull. *J. Acoust. Soc. Am.*, 103, 2403-10.

Thomas, J. L. & M. A. Fink (1996) Ultrasonic beam focusing through tissue inhomogeneities with a time reversal mirror: application to transskull therapy. *IEEE Trans. Ultrason. Ferroelectr. Freq. Control*, 43, 1122-1129.

Treece, G. M., A. H. Gee, P. M. Mayhew & K. E. Poole (2010) High resolution cortical bone thickness measurement from clinical CT data. *Med. Image. Anal.*, 14, 276-90.

White, P. J., G. T. Clement & K. Hynynen (2006) Longitudinal and shear mode ultrasound propagation in human skull bone. *Ultrasound Med. Biol.*, 32, 1085-96.

Therefore what is claimed is:

1. A method of intraoperatively reducing skull-induced aberrations during an intracranial focused ultrasound therapy procedure, the method comprising:
   after initiating delivery of focused ultrasound to an intracranial target within the cranial cavity of a subject using an array of ultrasound transducers:
   a) employing an ultrasound transducer of the array to transmit a non-therapeutic ultrasound pulse and receive a reflected ultrasound pulse associated with the reflection from skull surfaces within a local skull region adjacent to the ultrasound transducer, thereby obtaining a receive signal;
   b) determining a correction for correcting a therapeutic transmit signal delivered to the ultrasound transducer during subsequent focused ultrasound therapy, wherein the correction is suitable for reducing skull-induced aberrations associated with the local skull region, wherein the correction is determined by processing the receive signal and employing a skull thickness estimate associated with the local skull region, and wherein the skull thickness estimate is obtained based on previously measured volumetric image data associated with the subject;
   c) during the subsequent delivery of focused ultrasound to the subject, applying the correction to the therapeutic transmit signal provided to the ultrasound transducer, such that skull-induced phase aberrations are reduced; and
   d) while a temperature of the local skull region increases due to intracranial heating caused by the delivery of the focused ultrasound, repeating steps a) to c) one or more times to intermittently and intraoperatively recalculate the correction and apply the correction during subsequent delivery of focused ultrasound to dynamically correct for thermally-induced aberrations associated with local changes in the speed of sound in the skull due to spatially nonuniform increases in skull temperature.

2. The method according to claim 1 wherein steps a)-d) are performed to determine respective corrections for at least a subset of ultrasound transducers of the array.

3. The method according to claim 2 further comprising:
   processing the receive signal to determine that one or more measures associated with the receive signal satisfy exclusion criteria, and excluding the ultrasound transducer from use during subsequent delivery of focused ultrasound therapy by the array.

4. The method according to claim 3 wherein assessment of the exclusion criteria dependent on a signal-to-noise ratio of the receive signal.

5. The method according to claim 3 wherein assessment of the exclusion criteria is based on a presence of one or more spikes in a frequency spectrum of the receive signal.

6. The method according to claim 3 wherein the exclusion criteria is based on a comparison of the receive signal with one or more receive signals obtained from one or more neighbouring ultrasound transducers.

7. The method according to claim 3 wherein the exclusion criteria is based on a comparison of the receive signal with one or more receive signals obtained by scanning the ultrasound transducer.

8. The method according to claim 3 wherein the exclusion criteria is based on a measured incidence angle of the ultrasound transducer.

9. The method according to claim 1 further comprising: generating an additional correction for an additional ultrasound transducer based on respective corrections determined for one or more ultrasound transducers that are adjacent to the additional ultrasound transducer.

10. The method according to claim 1 wherein steps a)-d) a) e) are performed for all of the ultrasound transducers of the array.

11. The method according to claim 1 wherein when performing step b), the receive signal is processed in the frequency domain to identify resonant frequencies associated with the local skull region, and wherein a difference in resonant frequencies and the skull thickness estimate are employed when calculating the correction.

12. The method according to claim 1 wherein when performing step b), the receive signal is processed in the time domain using the pulse-echo method to determine a time delay associated with propagation through the local skull region, and wherein the time delay and the skull thickness estimate are employed when calculating the correction.

13. The method according to claim 1 wherein when performing step b), an incidence angle associated with the ultrasound transducer, relative an external skull surface corresponding to the local skull region, is employed when calculating the correction.

14. The method according to claim 13 wherein the incidence angle is determined by performing registration between a reference frame associated with the volumetric image data and an intraoperative reference frame.

15. The method according to claim 13 wherein the array of ultrasound transducers is supported by a patient-specific headset, wherein an incidence angle associated with a given ultrasound transducer of the array relative to the external skull surface is pre-configured based on an orientation of the given ultrasound transducer relative to the patient-specific headset.

16. The method according to claim 13 wherein the incidence angle associated with the ultrasound transducer is intraoperatively varied to maximize the receive signal for achieving normal incidence.

17. The method according to claim 16 wherein the incidence angle is varied by steering of the non-therapeutic ultrasound pulse.

18. The method according to claim 17 wherein the ultrasound transducer is a phased array ultrasound transducer and wherein the incidence angle is varied by electronic beam steering.

19. The method according to claim 17 wherein the ultrasound transducer is a single-element ultrasound transducer and wherein the incidence angle is varied mechanically.

20. The method according to claim 1 wherein the non-therapeutic ultrasound pulse is focused within the local skull region.

21. The method according to claim 1 wherein a center frequency of the non-therapeutic ultrasound pulse lies within the range of 400-600 KHz.

22. An intracranial focused ultrasound therapy system comprising:
an array of ultrasound transducers;
transducer driving circuitry operatively coupled to the array of ultrasound transducers; and
control and processing circuitry operatively coupled to the transducer driving circuitry, the control and processing circuitry comprising at least one processor and associated memory, the memory storing instructions executable by the at least one processor for performing operations comprising:
after initiating delivery of focused ultrasound to an intracranial target within the cranial cavity of a subject using the array of ultrasound transducers during a focused ultrasound therapy procedure:
a) employing an ultrasound transducer of the array to transmit a non-therapeutic ultrasound pulse and receive a reflected ultrasound pulse associated with the reflection from skull surfaces within a local skull region adjacent to the ultrasound transducer, thereby obtaining a receive signal;
b) determining a correction for correcting a therapeutic transmit signal delivered to the ultrasound transducer during subsequent focused ultrasound therapy, wherein the correction is suitable for reducing skull-induced aberrations associated with the local skull region, wherein the correction is determined by processing the receive signal and employing a skull thickness estimate associated with the local skull region, and wherein the skull thickness estimate is obtained based on previously measured volumetric image data associated with the subject; and
c) controlling the transducer driving circuitry such that the correction is applied to the transmit transducer provided to the ultrasound transducer when focused ultrasound therapy is subsequently delivered to the subject during the intracranial focused ultrasound therapy procedure; and
d) while a temperature of the local skull region increases due to intracranial heating caused by the delivery of the focused ultrasound, repeating steps a)-c) one or more times to intermittently and intraoperatively recalculate the correction apply the correction during subsequent delivery of focused ultrasound to dynamically correct for thermally-induced aberrations associated with local changes in the speed of sound in the skull due to spatially nonuniform increases in skull temperature.

* * * * *